(12) United States Patent
Bibi et al.

(10) Patent No.: US 7,823,590 B2
(45) Date of Patent: *Nov. 2, 2010

(54) DEVICES, FOR PREVENTING COLLAPSE OF THE UPPER AIRWAY, METHODS FOR USE THEREOF AND SYSTEMS AND ARTICLES OF MANUFACTURE INCLUDING SAME

(75) Inventors: Noam Bibi, Rehovot (IL); Nimrod Lev, Ganei Yehuda (IL)

(73) Assignee: Sleepup Ltd., Netanya (IL)

( * ) Notice: Subject to any disclaimer, the term of this patent is extended or adjusted under 35 U.S.C. 154(b) by 1579 days.

This patent is subject to a terminal disclaimer.

(21) Appl. No.: 10/859,339

(22) Filed: Jun. 3, 2004

(65) Prior Publication Data

US 2004/0237965 A1   Dec. 2, 2004

Related U.S. Application Data

(63) Continuation-in-part of application No. 10/270,507, filed on Oct. 16, 2002, now abandoned, and a continuation-in-part of application No. 10/103,915, filed on Mar. 25, 2002, now abandoned, which is a continuation-in-part of application No. 09/576,872, filed on May 22, 2000, now Pat. No. 6,371,112.

(51) Int. Cl.
  *A62B 18/08* (2006.01)
  *A61M 16/00* (2006.01)
(52) U.S. Cl. .................. 128/206.29; 128/200.26
(58) Field of Classification Search .............. 128/848, 128/859–861, 206.21, 206.27, 206.28, 206.29, 128/200.26

See application file for complete search history.

(56) References Cited

U.S. PATENT DOCUMENTS

| 4,198,967 | A |   | 4/1980  | Dror |          |
|-----------|---|---|---------|------|----------|
| 4,298,023 | A |   | 11/1981 | McGinnis |      |
| 4,513,741 | A |   | 4/1985  | Demi |          |
| 4,676,240 | A |   | 6/1987  | Gardy |         |
| 5,195,513 | A | * | 3/1993  | Sinko et al. | 128/200.26 |
| 5,431,158 | A | * | 7/1995  | Tirotta | 128/206.21 |
| 5,462,050 | A | * | 10/1995 | Dahlstrand | 128/207.18 |

(Continued)

OTHER PUBLICATIONS

Guilleminault and M. Partinen (eds.) (1990) "Obstructive Sleep Apnea Syndrome: Clinical; Research and Treatment". Raven Press, New York, NY, USA, pp. xv-xvii.

(Continued)

*Primary Examiner*—Justine R Yu
*Assistant Examiner*—Kristen C Matter
(74) *Attorney, Agent, or Firm*—Mark M. Friedman

(57) ABSTRACT

Devices and methods to prevent airway collapse are disclosed. The device includes a mouthpiece featuring a positioning aid adjustable by inflation accomplished via a gas exchange port attachable to a source of pressure and a breathing tube. Inflation causes an asymmetric protrusion on the mouthpiece, preferably above the breathing tube so that the positioning aid fits into the roof of the mouth. Preferably, tongue movement is at least partially restricted. An additional device featuring a wearable battery operated compressor is further disclosed. A device in the form of a pacifier is disclosed as a preferred embodiment for use in young patients. Preferably, devices are supplied as articles of manufacture. Use of disclosed devices constitute methods of preventing collapse of the upper airway.

21 Claims, 18 Drawing Sheets

U.S. PATENT DOCUMENTS

| | | | |
|---|---|---|---|
| 5,649,540 | A | 7/1997 | Alvarez et al. |
| 5,871,011 | A * | 2/1999 | Howell et al. .......... 128/206.22 |
| 5,950,624 | A * | 9/1999 | Hart ...................... 128/207.15 |
| 6,371,112 | B1 | 4/2002 | Bibi |
| 6,536,432 | B2 * | 3/2003 | Truschel ................ 128/205.23 |
| 2003/0079751 | A1 * | 5/2003 | Kwok .................... 128/206.15 |

OTHER PUBLICATIONS

Levitzki MG (eds)(1986) "Pulmonary Physiology" McGraw—Hill Book Company, New York, NY, USA pp. 37-40.

C.E. Sullivan et al., in C. Guilleminault and M. Partinen, Ibid., pp. 49-69.

S.T. Kuna et al. (1991) JAMA 266:1384-1389.

J.E. Remmers et al., (1978) J. Appl. Physiol. 44:931-938.

D.J. Tangel et al. (1991) J. Appl. Physiol. 70:2574-2581.

M. Partinen et al. (1988) Chest 94: 1200-1204.

Je et al. (1988) Chest 94:9-14.

Young et al. (1997) Sleep 20:705-706).

C.E. Sullivan et al. (1981) Lancet 1:862-865; M.H. Sanders et al. (1983) Chest 83:144-145.

Hedner et al. (1995) Eur. Respir. J. 8:222-229; C. Jenkinson et al. (1999) Lancet 353: 2100-2105).

N.P. Kribbs et al. (1993) Am. Rev. Respir. Dis. 147:887-895.

Rauscher et al. (1993) Chest 103:1675-1680.

Shannon DC In: Disorders of the Respiratory Tract in Children- SIDS and Apnea in infancy Kendig & Chernick Eds (1990)W.B. Saunders Company, Philadelphia, PA, USA pp. 939-952.).

Tonkin S. (1975) Pediatrics 55:650-654.

Swift PGF et al (1973) Arch Dis Child 48:947-950.

C. Guilleminault and E. Largesi (eds.) (1983) Raven Press, New York, NY, USA, pp. 107-125.

* cited by examiner

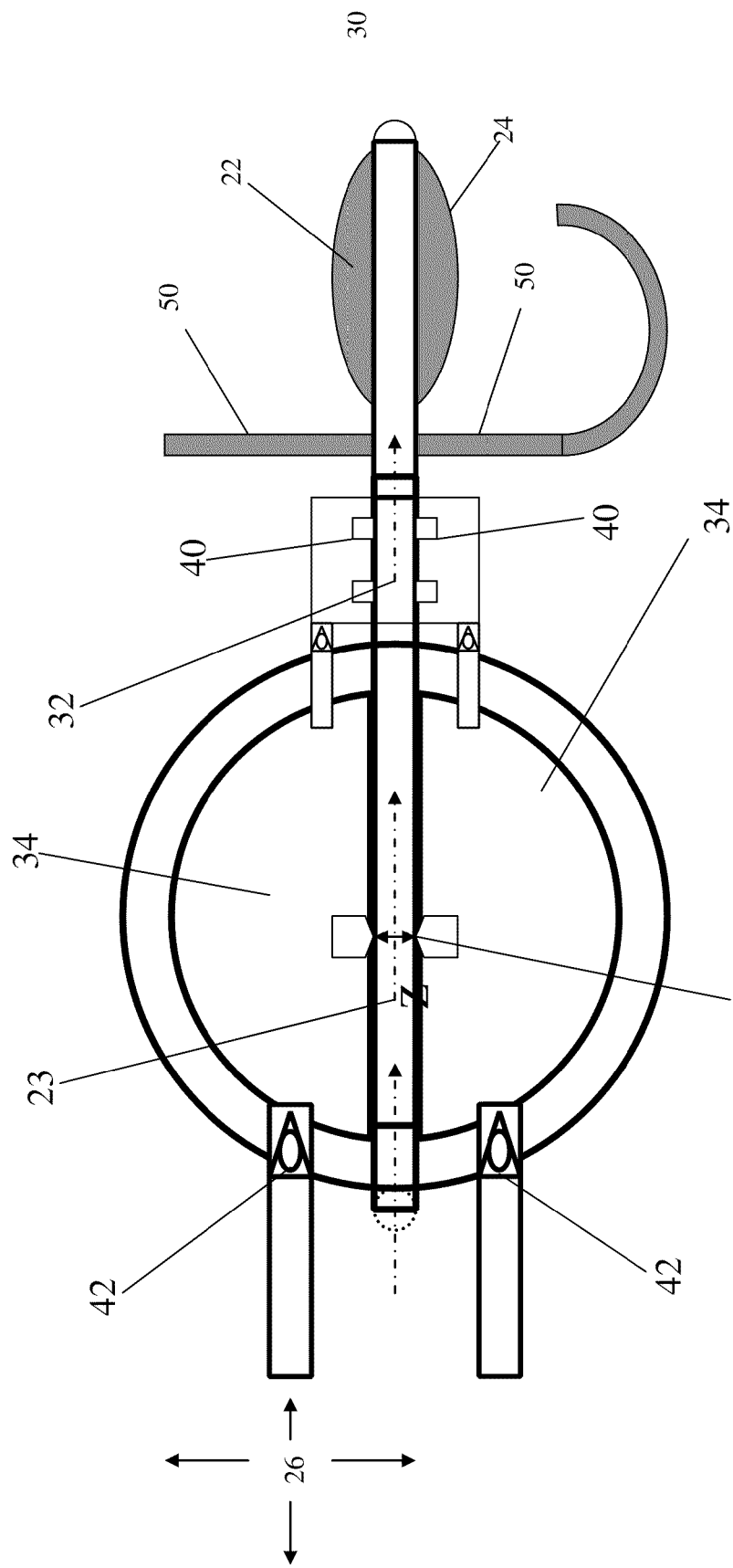

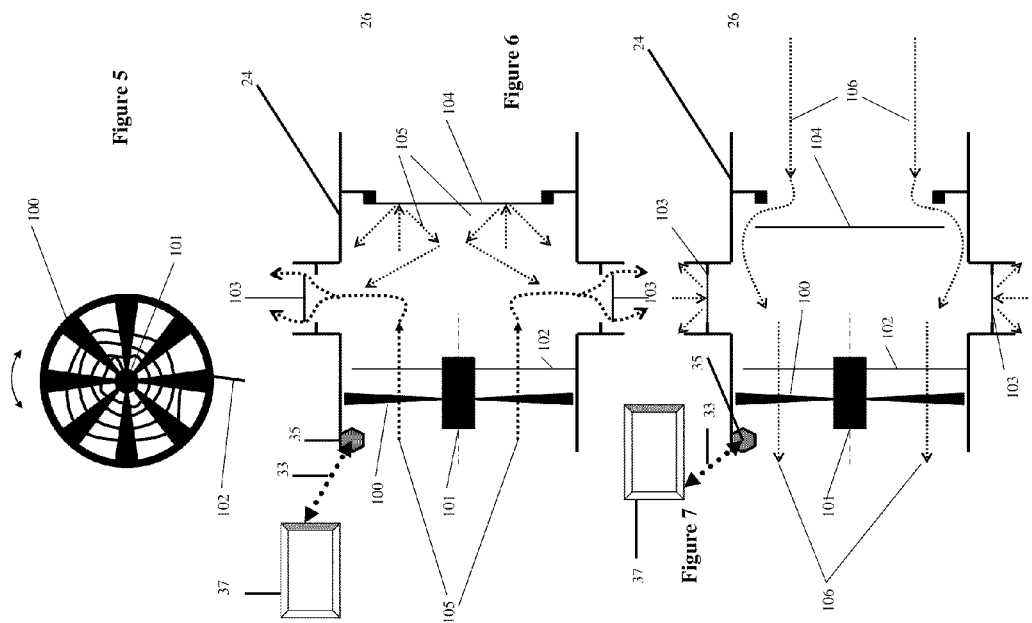

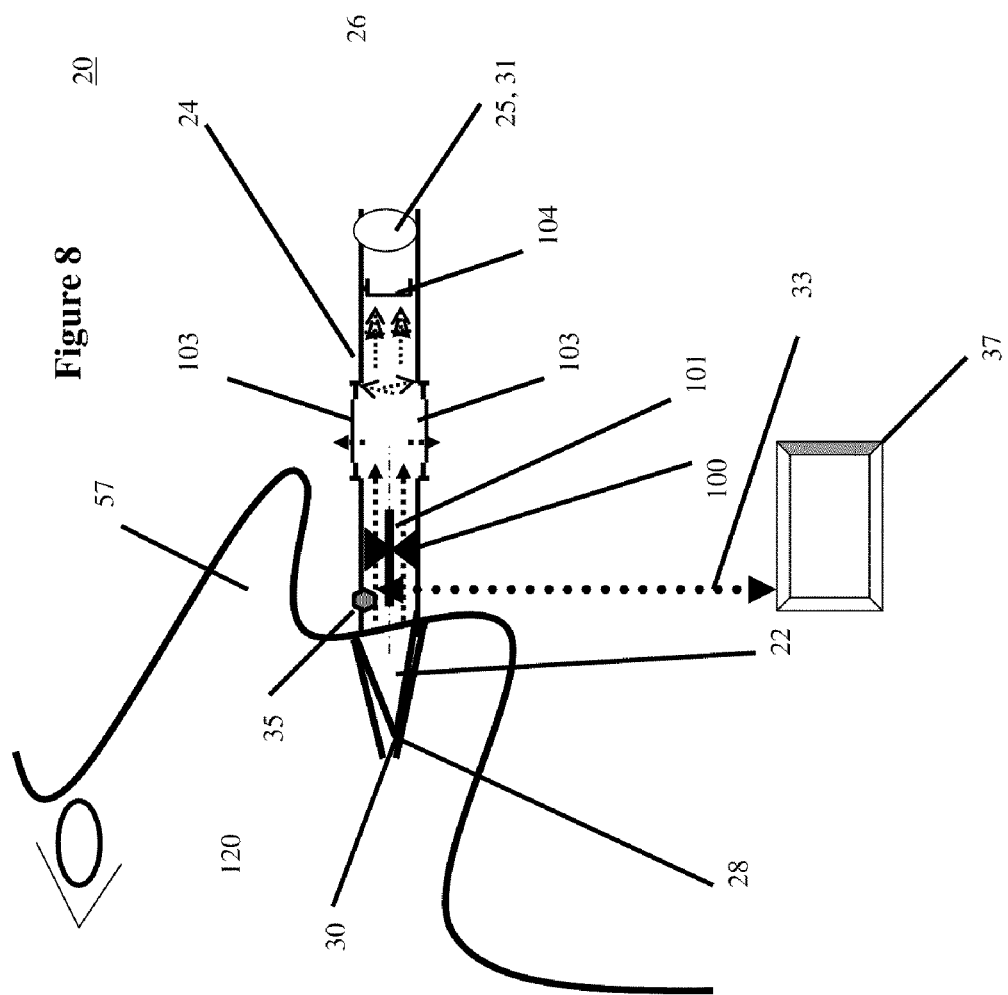

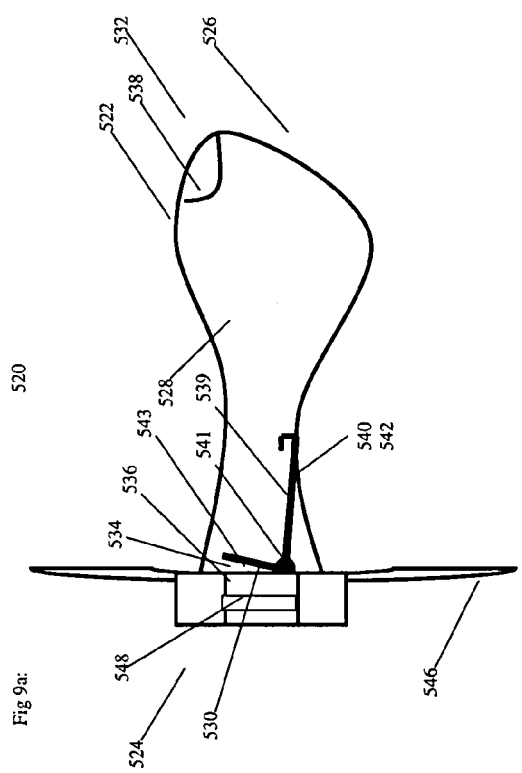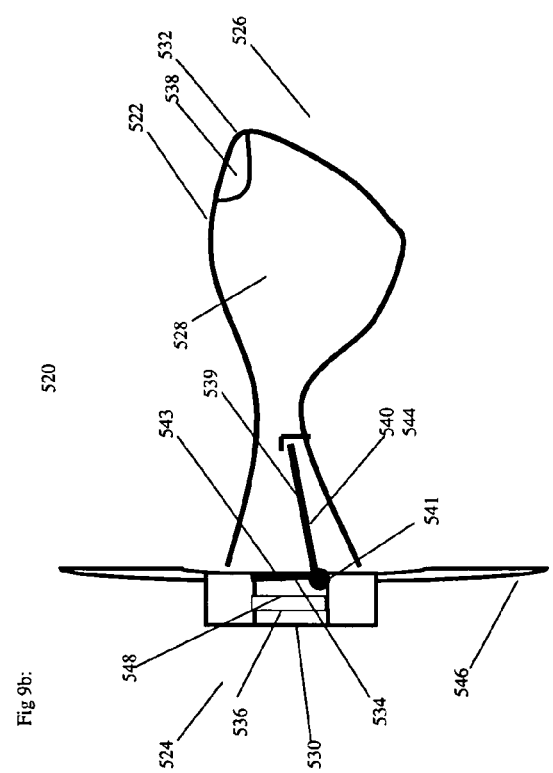

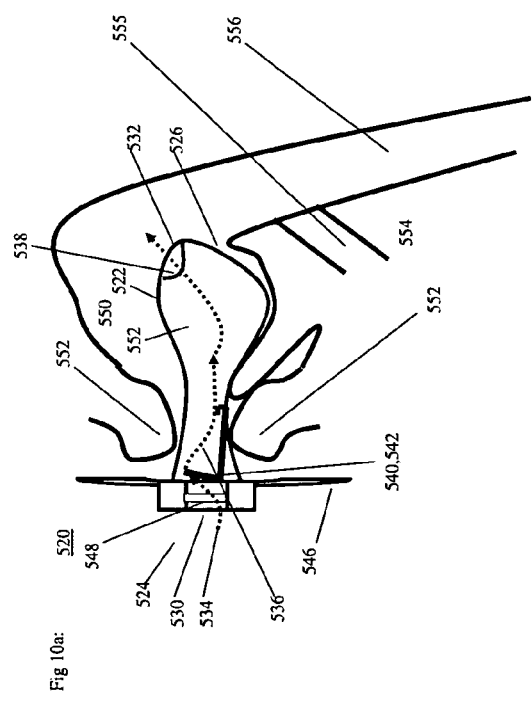
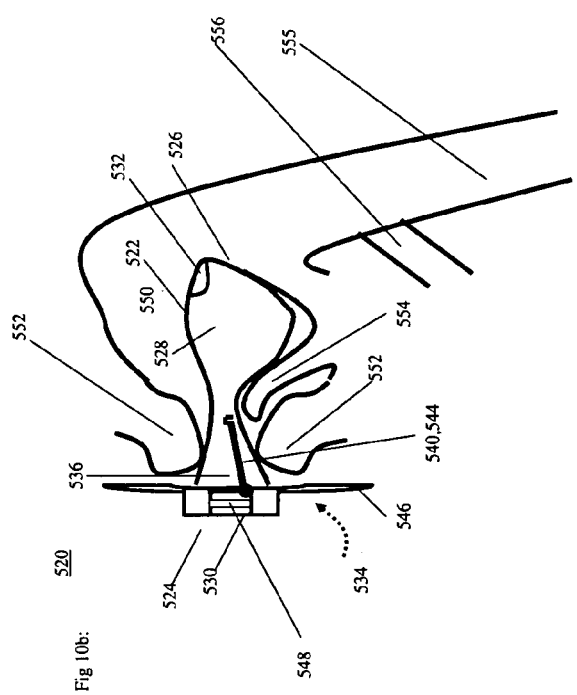
Fig 10a:
Fig 10b:

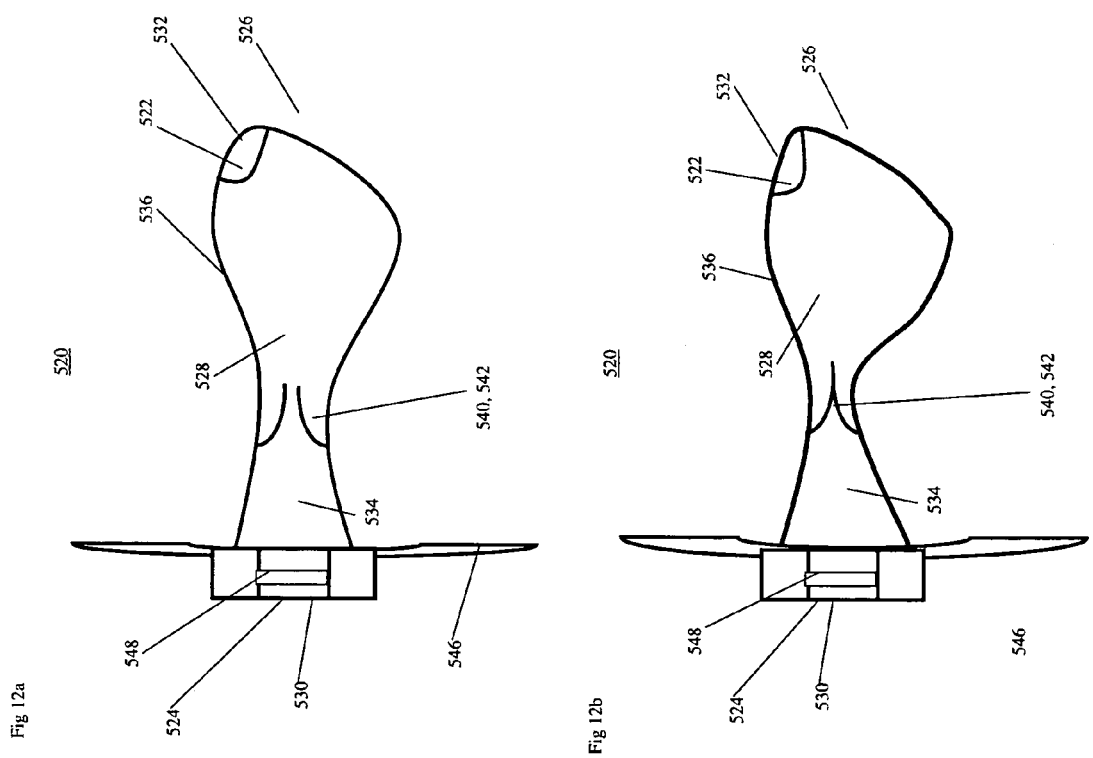

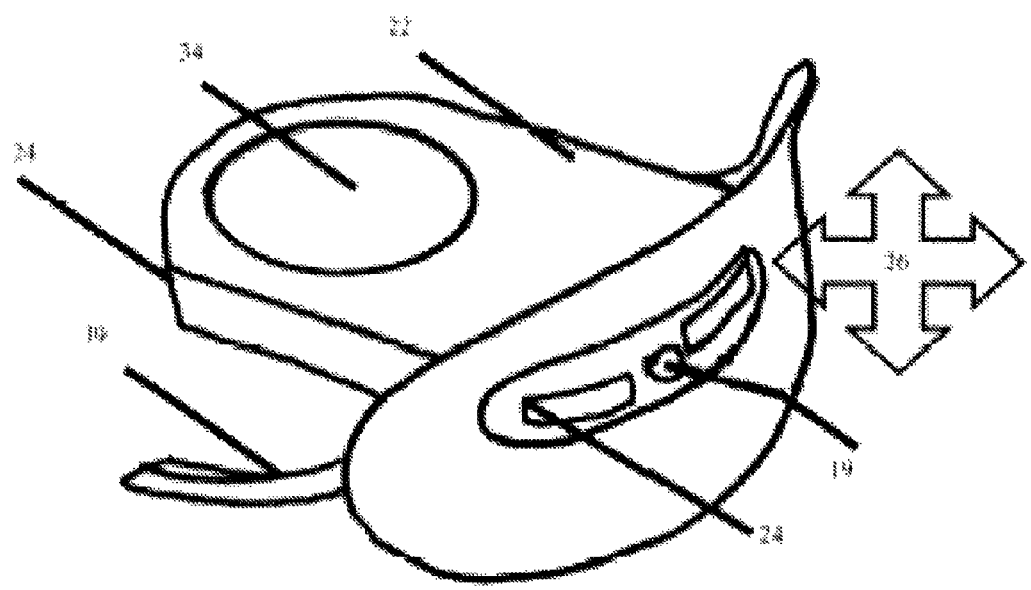

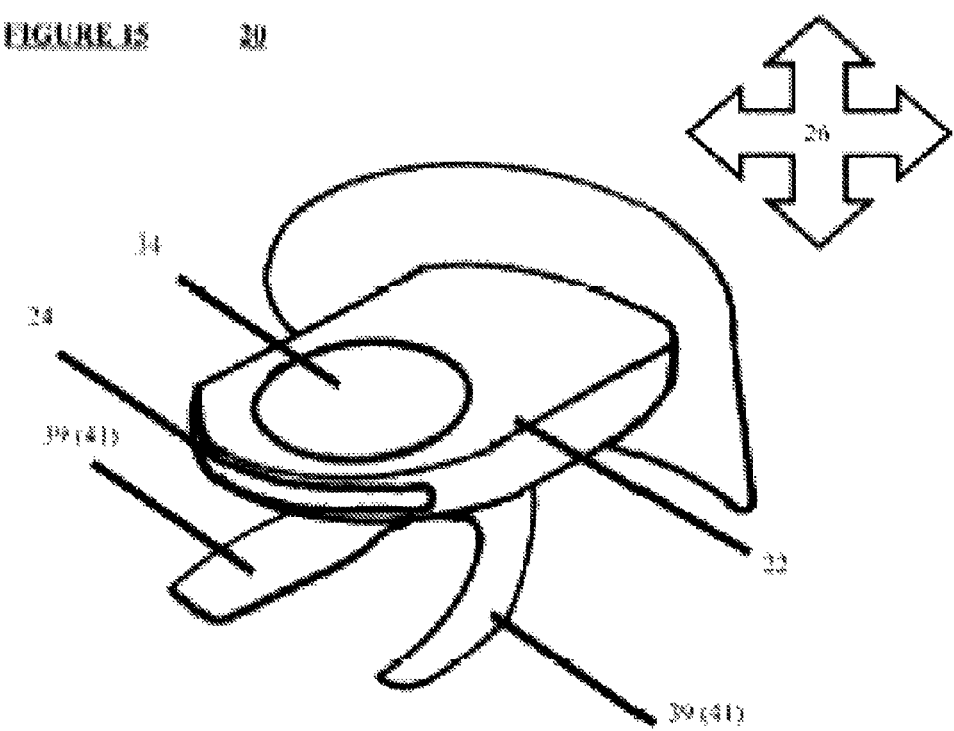

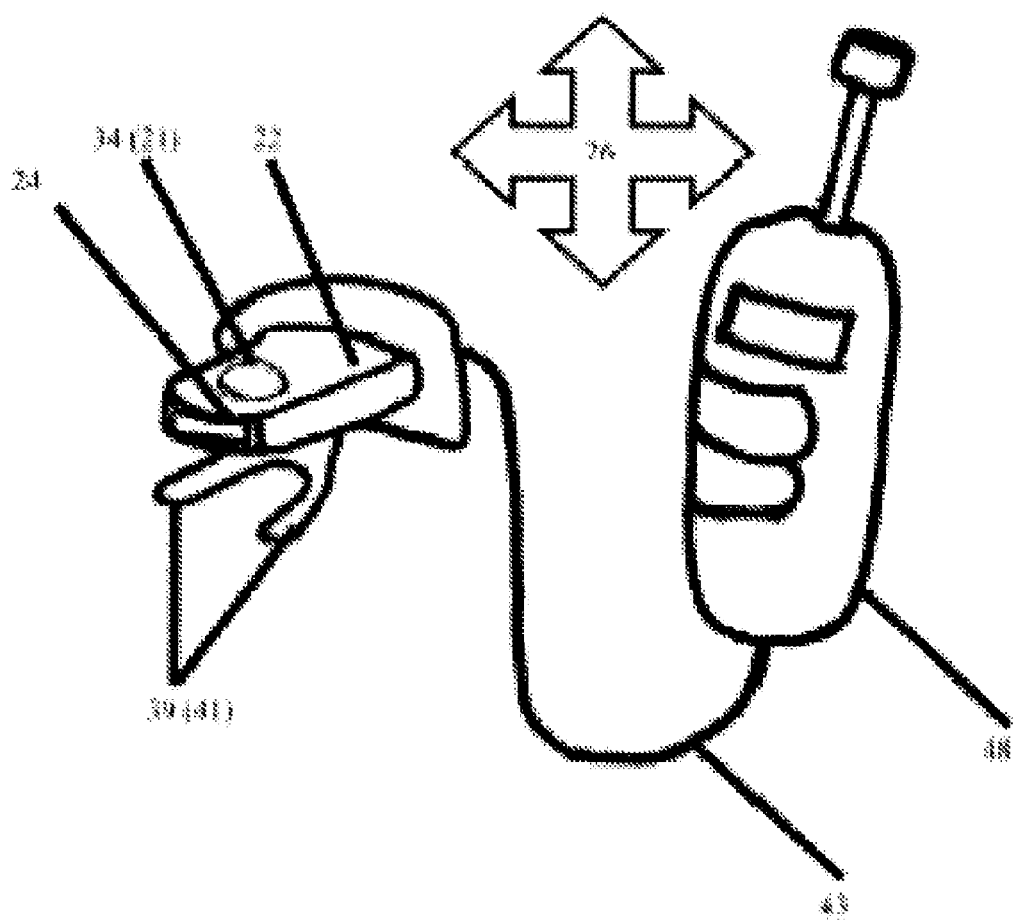

FIGURE 17    70
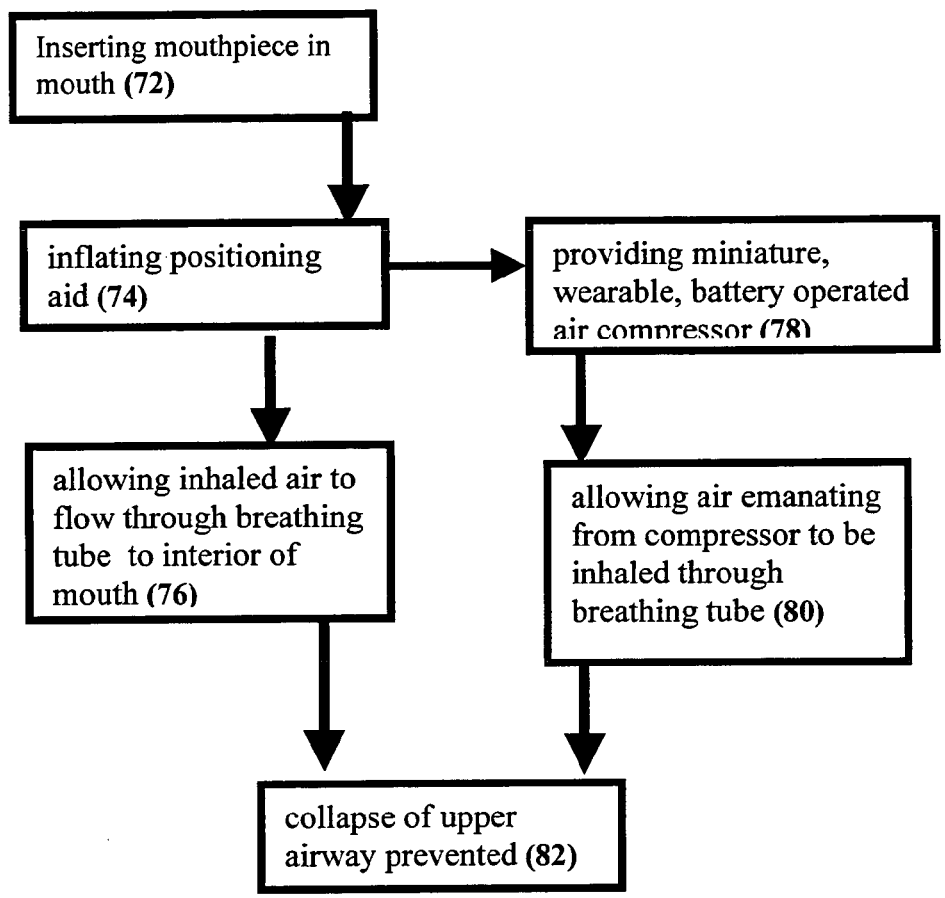

DEVICES, FOR PREVENTING COLLAPSE OF THE UPPER AIRWAY, METHODS FOR USE THEREOF AND SYSTEMS AND ARTICLES OF MANUFACTURE INCLUDING SAME

This application is a Continuation-in-Part of U.S. patent application Ser. No. 10/270,507 filed 16 Oct. 2002, currently abandoned, and U.S. patent application Ser. No. 10/103,915 filed 25 Mar. 2002, abandoned, which is Continuation-in-Part of U.S. patent application Ser. No. 09/576,872 filed 22 May, 2000 issued as U.S. Pat. No. 6,371,112 on Apr. 16, 2002.

FIELD AND BACKGROUND OF THE INVENTION

The present invention relates to devices for preventing collapse of the upper airway, methods for use thereof and systems and articles of manufacture including same. More particularly, the present invention relates to the use thereof for treatment of breathing disorders including, but not limited to, obstructive sleep apnea (OSA), apnea of infancy (AOI), sudden infant death syndrome (SIDS) and snoring. The present invention is further of devices, systems and methods which monitor parameters of air exhaled by a patient through such a device and of a physiologic status of a patient breathing through such a device. Devices of the present invention may, in some cases, take the form of a pacifier.

OSA is a syndrome with significant morbidity and mortality (C. Guilleminault and M. Partinen (eds.) (1990) "Obstructive Sleep Apnea Syndrome: Clinical; Research and Treatment". Raven Press, New York, N.Y., USA, pp xv-xvii). OSA is caused by repeated collapse of soft tissues forming the walls of the upper airway in the sub-glottal region during sleep (C. Guilleminault and M. Partinen, Ibid.). Opening of this portion of the airway depends upon the balance between negative pressure, which is at least −7 or −10 cm $H_2O$ in normal quiet breathing (Levitzki MG (eds)(1986) "Pulmonary Physiology" McGraw—Hill Book Company, New York, N.Y., USA pp 37-40) outside the cavity caused by muscular action during breathing (e.g. action of the diaphragm and muscles surrounding the rib cage) and muscle tone in the upper airway itself (C. E. Sullivan et al., in C. Guilleminault and M. Partinen, Ibid., pp 49-69; S. T. Kuna et al. (1991) JAMA 266:1384-1389; J. E. Remmers et al., (1978) J. Appl. Physiol. 44:931-938; and D. J. Tangel et al. (1991) J. Appl. Physiol. 70:2574-2581). This repeated collapse of the upper airway causes a decrease in blood oxygen saturation which leads to sleep disturbances, fatigue and a general feeling of malaise in affected patients.

OSA is a common disorder with an estimated 2% of women and 4% of men being affected to a degree that treatment is advisable. This means that an estimated 12 to 18 million patients are affected in the USA. Since only about 7% to 18% of the population has been tested for this disorder, these estimates should be viewed as minimum estimates (C. Guilleminault in C. Guilleminault and E. Largesi (eds.) (1983) Raven Press, New York, N.Y., USA, pp 107-125; M. Partinen et al. (1988) Chest 94: 1200-1204; J. JE et al. (1988) Chest 94:9-14; National Commission on Sleep Disorders Research (1995) "Wake Up America: A National Sleep Alert" US Government Printing Office, Washington, D.C., USA, pp 2-10; T. Young et al. (1997) Sleep 20:705-706).

Currently accepted treatment for OSA typically includes continuous positive airway pressure (CPAP). CPAP, as currently practiced, involves connection of a pressurized air delivering device to the mouth or nose of the patient. This device typically is connected to a pressurized air source in the form of a compressor or tank with a regulator. These pressurized air supplies are expensive, large, and noisy.

Delivery of a constant flow of a breathable gas mixture through the device maintains a constant positive pressure in the upper airway. This constantly applied pressure prevents the collapse of the airway described hereinabove (C. E. Sullivan et al. (1981) Lancet 1:862-865; M. H. Sanders et al. (1983) Chest 83:144-145). CPAP is effective in treating OSA by preventing collapse of the airway and associated tiredness, fatigue, diminished intellectual function, and snoring and can even lengthen patient life expectancy (J. Hender et al. (1995) Eur. Respir. J. 8:222-229; H. Minemura et al. (1998) Intern. Med. 37: 1009-1013; C. Jenkinson et al. (1999) Lancet 353: 2100-2105).

In order to keep the pressure in the airway constant during inhalation and exhalation, a pressure valve is sometimes incorporated into the pressurized air delivering device. One such valve is taught by U.S. Pat. No. 4,298,023 for a spring loaded exhalation valve. Teachings of this patent specifically relate to treatment regimens which include a flow of gas delivered to the airway from a pressurized air supply.

However, patient compliance with CPAP treatment regimens is typically poor despite the proven efficacy of the treatment. Research suggests that 60 to 70% compliance is the norm and that the average patient use of CPAP is limited to 5 hours per night (N. P. Kribbs et al. (1993) Am. Rev. Respir. Dis. 147:887-895; H. Rauscher et al. (1993) Chest 103:1675-1680). In addition, many patients never begin treatment at all owing to the high cost of CPAP equipment.

Currently accepted treatment for AOI typically includes continuous positive airway pressure (CPAP). CPAP, as currently practiced, involves connection of a pressurized air-delivering device to the mouth or nose of the patient. This device typically is connected to a pressurized air source in the form of a compressor or tank with a regulator. These pressurized air supplies are expensive, large, and noisy.

Delivery of a constant flow of a breathable gas mixture through the device maintains a constant positive pressure in the upper airway. This constantly applied pressure prevents the collapse of the airway described hereinabove (C. E. Sullivan et al. (1981) Lancet 1:862-865; M. H. Sanders et al. (1983) Chest 83:144-145). CPAP is effective because it prevents collapse of the airway and associated tiredness, fatigue, diminished intellectual function, and snoring and can even lengthen patient life expectancy (J. Hender et al. (1995) Eur. Respir. J. 8:222-229; C. Jenkinson et al. (1999) Lancet 353: 2100-2105).

However, patient compliance with CPAP treatment regimens is typically poor despite the proven efficacy of the treatment. Research suggests that 60 to 70% compliance is the norm and that the average patient use of CPAP is limited to 5 hours per night (N. P. Kribbs et al. (1993) Am. Rev. Respir. Dis. 147:887-895; H. Rauscher et al. (1993) Chest 103:1675-1680). In addition, many patients never begin treatment at all owing to the high cost of CPAP equipment. Further, infants and children are less likely to comply than adults because they are incapable of understanding the need for treatment. Parents of these young patients are often disturbed by the "medical" appearance of conventional CPAP equipment and find it embarrassing to show to relatives and caregivers.

Further, sleep apnea in infants and young children is often treated by surgical intervention. Such intervention necessarily includes all of the risks associated with anesthesia and surgery.

Infants are typically obligatory nasal breathers (Shannon DC In: Disorders of the Respiratory Tract In Children—SIDS and Apnea in infancy Kendig & Chernick Eds (1990) W. B. Saunders Company, Philadelphia, Pa., USA pp 939-952.). Any change in airflows in the upper airways increase vulnerability to inadequate ventilation because: (1). the hypopharynx is shallow; (2) the tongue and epiglottis are more cephaled and (3) the mandible is more mobile (Tonkin S. (1975) Pediatrics 55:650-654). Normal infants typically have difficulty responding to nasal occlusion. Studies show that 44% of 6 week old infants struggled but failed to establish an oral airway when the nostrils were pinched for 25 seconds (Swift PGF et al (1973) Arch Dis Child 48:947-950). The physiologic basis for the failure to maintain adequate oral ventilation during occlusion in both normal and at risk infants is unknown. This mechanism has been suggested as a cause of AOI which can lead to SIDS (Anderson RB et al (1971) Biol Neonate 18:395-398.

U.S. Pat. No. 4,513,741 to Demi discloses an apparatus including a breathing tube and inflatable mouthpiece designed and constructed for use in animals, especially animals with an elongated snout. Demi neither hints nor suggests that the disclosed apparatus is useful or efficacious in treatment of sleep disorder such as AOI, SDS, or snoring. Further, the apparatus disclosed by Demi is wholly incompatible with human facial anatomy.

Thus, infants and young children suffering from excess nasal secretion tend to reject a pacifier during sleep in an effort to establish an alternate airway. This rejection may lead to sleep interruption when the comfort of sucking is subsequently missed.

There is thus a widely recognized need for, and it would be highly advantageous to have, devices for preventing collapse of the upper airway, methods for use thereof and systems and articles of manufacture including same. which are devoid of the above limitations. Further, monitoring of a parameter of exhaled air or patient physiology by such a device, system or method would increase utility thereof.

SUMMARY OF THE INVENTION

According to one aspect of the present invention there is provided a self contained CPAP device. The device comprises; (a) a mouthpiece insertable in a mouth of a patient; (b) a breathing tube connecting between an outside environment and an interior of the mouth, the breathing tube containing at least one bi-directional pressure sensitive valve therein; (c) at least one inflatable body, the inflatable body functioning to adjust an internal cross sectional area of the breathing tube during a process of respiration;

According to another aspect of the present invention there is provided a system for prophylactic treatment of a breathing disorder, the system comprising a miniature CPAP device, the device being designed and constructed to maintain sufficient pressure in an upper airway of a patient such that collapse thereof is prevented;

According to yet another aspect of the present invention there is provided an improved method of preventing a breathing disorder by means of CPAP, the method comprising the steps of: (a) inserting a mouthpiece in a mouth of a patient; (b) (c) adjusting an internal cross sectional area of the breathing tube during a process of respiration by means of at least one inflatable body, the at least one inflatable body serving to regulate an air pressure within the mouth during the process of respiration and (d)

According to further features in preferred embodiments of the invention described below, the at least one inflatable body comprises: (i) at least one elastic balloon; (ii) at least one first unidirectional pressure sensitive valve in communication an interior of the breathing tube;

According to still further features in the described preferred embodiments the mouthpiece is adjustable to fit the mouth of the patient.

According to still further features in the described preferred embodiments there is provided a mechanism for facilitating inflation of the mouthpiece.

According to still further features in the described preferred embodiments there is provided a mechanism for sealing between the mouthpiece and lips of the patient, such that airflow between the lips and the mouthpiece is diminished.

According to still further features in the described preferred embodiments the device further comprises a chin holder having a first end which is capable of engaging a chin of the patient and a second end which is connectable to the device.

According to still further features in the described preferred embodiments the breathing tube passes through the mouthpiece According to still further features in the described preferred embodiments the device further comprises at least one retaining piece for holding the device in place.

According to still further features in the described preferred embodiments the at least one retaining piece includes at least one item selected from the group consisting of at least one strap, at least one elastic band, at least one piece of Velcro™ and a pair of protrusions which engage the ears of the patient.

According to still further features in the described preferred embodiments the device further comprises a filter in the breathing tube, the filter designed and constructed to prevent the entry of foreign bodies thereto.

According to still further features in the described preferred embodiments the device is designed and configured for a purpose selected from the group consisting of treating obstructive sleep apnea, treating apnea of infancy and preventing sudden infant death syndrome.

According to still further features in the described preferred embodiments the device comprises: (i) a mouthpiece insertable in a mouth of a patient; (ii) a breathing tube connecting between an outside environment and an interior of the mouth, the breathing tube containing at least one bi-directional pressure sensitive valve therein; (iii) an inflatable body, the inflatable body functioning to adjust an internal cross sectional area of the breathing tube during a process of respiration, (and (iv) a mask, being designed and constructed to cover a nose of the patient, We might have a mask, but I'm not sure we'll use it to route "used" air (exhaled air) back to the nose . . .

Same as before—it's a re-breathing mechanism we neglected already.

According to still further features in the described preferred embodiments the method comprises the additional step of adjusting the mouthpiece to fit the mouth of the patient.

According to still further features in the described preferred embodiments the step of adjusting is accomplished by inflating an inflatable part of the mouthpiece.

According to another aspect of the present invention there is provided a device for preventing collapse of the upper airway. The device includes a mouthpiece insertable in a mouth of a patient and a breathing tube connecting between an outside environment and an interior of the mouth. The last 3 paragraphs describe the same device but it looks like 2 different ones. Can you edit it in a way it will be understood it's the same device?

According to yet another aspect of the present invention there is provided a method of preventing collapse of the upper airway. The method includes the steps of: (a) inserting a mouthpiece in a mouth of a patient; and (b) adjusting it to the patient mouth by inflation of inflatable balloon and (c) allowing inhaled air to flow through a breathing tube connecting between an outside environment and an interior of the mouth.

According to still another aspect of the present invention there is provided a system for prophylactic treatment of a breathing disorder. The system includes a miniature CPAP device. The device is designed and constructed to maintain sufficient pressure in an upper airway of a patient such that collapse thereof is prevented while functioning independently of any item selected from the group consisting of, a pressurized gas cylinder and an electro-hydrolytic oxygen source. The system includes: (i) a mouthpiece insertable in a mouth of a patient; (ii) a breathing tube connecting between an outside environment and an interior of the mouth, the breathing tube containing at least one bi-directional pressure sensitive valve therein; and (iii) a miniature, battery operated compressor.

According to an additional aspect of the present invention there is provided an improved method of preventing a breathing disorder by means of CPAP. The method includes the steps of: (a) inserting a mouthpiece in a mouth of a patient; (b) allowing inhaled air to flow through at least one bi-directional pressure sensitive valve contained within a breathing tube connecting between an outside environment and an interior of the mouth; and (c) providing a battery operated compressor According to yet another additional aspect of the present invention there is provided a system for prophylactic treatment of a breathing disorder, the system includes a battery operated CPAP device. The device is designed and constructed to maintain sufficient pressure in an upper airway of a patient such that collapse thereof is prevented while functioning independently of any item selected from the group consisting of a mains dependent pump, a mains dependent compressor, a pressurized gas cylinder and an electro-hydrolytic oxygen source. The device includes: (i) a mouthpiece insertable in a mouth of the patient (adjustable?); (ii) a breathing tube connecting between an outside environment and an interior of the mouth, the breathing tube containing (at least one bi-directional pressure sensitive valve therein?); (iii) at least one inflatable body, the at least one inflatable body functioning to adjust an internal cross sectional area of the breathing tube during a process of respiration, (iv) a mask, the mask being in fluid communication with the mouthpiece and being designed and constructed to cover a nose of the patient; and (v) a sensor designed and constructed to measure a parameter selected from the group consisting of an air parameter and a patient parameter. For purposes of this specification and the accompanying claims, the term "sensor" refers equally to a single sensor or a combination of sensors capable of measuring, separately or in concert, at least one air or patient parameter or a combination thereof.

According to still further features in the described preferred embodiments the device further includes a humidifying element designed and constructed to add moisture to inhaled air According to still further features in the described preferred embodiments the device further includes a sensor in the breathing tube, the sensor designed and constructed to measure a parameter selected from the group consisting of an air parameter and a patient parameter.

According to still further features in the described preferred embodiments the method further includes covering a nose of the patient with a mask, the mask being in fluid communication with Mouthpiece.

According to still further features in the described preferred the sensor resides at a location selected from the breathing tube and the inflatable body.

According to an additional aspect of the present invention there is provided an improved pacifier. The pacifier includes: (a) an artificial nipple designed and constructed to stimulate sucking when inserted in a mouth of a young patient, the artificial nipple having a proximal portion insertable in the mouth and a distal portion protruding therefrom, the artificial nipple being hollow and includes an interior volume serving as a first channel of fluid communication between at least one first aperture and at least one second aperture; (b) the at least one first aperture forming a second channel of fluid communication between the interior volume of the artificial nipple and the mouth of the young patient; (c) the at least one second aperture forming a third channel of fluid communication between the interior volume of the artificial nipple and an outside environment; and (d) an air flow valve having a first operational state in which the first channel of fluid communication is closed and a second operational state on which the first channel of fluid communication is open. The pacifier is constructed so that sucking causes the air flow valve to assume the first operational state while cessation of sucking allows the air flow valve to assume the second operational state.

According to another additional aspect of the present invention there is provided a method of facilitating mouth breathing in a young patient. The method includes: (a) providing an artificial nipple designed and constructed to stimulate sucking when inserted in a mouth of a young patient, the artificial nipple having a proximal portion insertable in the mouth and a distal portion protruding therefrom, the artificial nipple being hollow and includes an interior volume, the artificial nipple further includes at least one first aperture and at least one second aperture so that a channel of fluid communication exists between an outside environment and the mouth of the young patient, the channel of fluid communication including at least a portion of the interior volume and (b) regulating a flow of air in the channel of fluid communication by means of an air flow valve having a first operational state in which the channel of fluid communication is closed and a second operational state on which the channel of fluid communication is open.

According to the method, sucking causes the air flow valve to assume the first operational state while cessation of sucking allows the air flow valve to assume the second operational state. Thus, it will be appreciated that the phrase "young patient", as used herein and in the accompanying claims, refers to a patient that habitually uses a pacifier as a means of relaxation. This habitual pacifier use may occur, for example, during sleep.

According to further features in the described preferred embodiments the improved pacifier further includes a retention guard designed and constructed to prevent swallowing of the artificial nipple. The retention guard may be, for example, attached to or integrally formed with the distal portion of the artificial nipple According to still further features in the described preferred embodiments the improved pacifier further includes a filter designed and constructed to prevent the entry of foreign bodies thereto. The filter may be located, for example, in proximity to the at least one second aperture.

According to still further features in the described preferred embodiments the method further includes employing a retention guard designed and constructed to prevent swallowing of the artificial nipple, the retention guard being attached to or integrally formed with the distal portion of the artificial nipple According to still further features in the described preferred embodiments the method further includes preventing the entry of foreign bodies into the channel of fluid communication by means of a filter located in proximity to the at least one second aperture.

According to one aspect of the present invention there is provided a device for preventing collapse of the upper airway in a human subject. The device includes: (a) a mouthpiece insertable in a mouth of a human subject, (b) an inflatable positioning aid adjustable to fit the mouth by inflation, the inflation accomplished by means of a gas exchange port providing a regulatable channel of fluid communication between the inflatable positioning aid and an external source of positive pressure, the positioning aid attached to or integrally constructed with the mouthpiece, wherein inflation of the positioning aid causes an asymmetric protrusion of the positioning aid from the mouthpiece; and (c) a breathing tube connecting between an outside environment and an interior of the mouth. When used, the device prevents collapse of the upper airway of the human subject. The asymmetric protrusion is preferably above the breathing tube so that the positioning aid fits into the roof of the mouth. Preferably, tongue movement is at least partially restricted.

According to another aspect of the present invention there is provided a method of preventing collapse of the upper airway in a human subject. The method includes the steps of: (a) inserting a mouthpiece in a mouth of the human subject; and (b) inflating an inflatable positioning aid adjustable to fit the mouth by inflation, the inflating accomplished by means of a gas exchange port providing a regulatable channel of fluid communication between the inflatable positioning aid and an external source of positive pressure, the positioning aid attached to or integrally constructed with the mouthpiece, wherein inflation of the positioning aid causes the mouthpiece to be engaged and retained in a desired position in an interior of the mouth by means of an asymmetric protrusion of the positioning aid from the mouthpiece; and (c) allowing inhaled air to flow through a breathing tube connecting between an outside environment and an interior of the mouth so that collapse of the upper airway of the human subject is prevented.

According to yet another aspect of the present invention there is provided an article of manufacture. The article of manufacture includes: (a) a device for preventing collapse of the upper airway in a human subject essentially as described hereinabove and hereinbelow; (b) packaging material; and (c) instructions for use identifying the device as efficacious in preventing collapse of the upper airway of the human subject.

According to still another aspect of the present invention there is provided a system for prophylactic treatment of a breathing disorder. The system includes a miniature CPAP device including: (a) a mouthpiece insertable in a mouth of a patient; (b) a miniature, wearable, battery operated air compressor; and (c) a breathing tube connecting between the miniature, wearable, battery operated air compressor and an interior of the mouth of the patient. The miniature, wearable, battery operated air compressor is capable of maintaining sufficient pressure in an upper airway of the patient that collapse thereof is prevented.

According to an additional aspect of the present invention there is provided an improved method of preventing a breathing disorder by means of CPAP. The method includes the steps of: (a) inserting a mouthpiece in a mouth of a patient; (b) providing a miniature, wearable, battery operated air compressor connectable to a breathing tube connecting between the miniature, wearable, battery operated air compressor and an interior of the mouth of the patient, the breathing tube containing at least one bi-directional pressure sensitive valve therein; and (c) allowing at least a portion of a flow of air emanating from the miniature, wearable, battery operated air compressor to be inhaled through the at least one bi-directional pressure sensitive valve contained within the breathing tube; wherein a breathing pattern of the patient at least partially regulates a net airflow in an upper airway of the patient.

According to further features in preferred embodiments of the invention described below, the breathing tube passes through the mouthpiece.

According to still further features in the described preferred embodiments a filter in the breathing tube is further included. The filter is designed and constructed to prevent the entry of foreign bodies into the breathing tube.

According to still further features in the described preferred embodiments a humidifying element designed and constructed to add moisture to inhaled air is further included.

According to still further features in the described preferred embodiments the filter further functions as a humidifying element. To that end, the filter may, for example, retain moisture from exhaled air and transferring the moisture to air which is subsequently inhaled.

According to still further features in the described preferred embodiments a sensor in the breathing tube is further included. The sensor serves to measure at least one parameter selected from the group consisting of an air parameter and a patient parameter.

According to still further features in the described preferred embodiments at least one support member positionable beneath a tongue of the human subject is further included. The support member functions to aid the human subject in maintaining a correct position of the device during use. The support member may be attached to or integrally formed with, the mouthpiece.

According to still further features in the described preferred embodiments the at least ones support member is at least partially constructed of a flexible material. The phrase "flexible material" as used in this specification and the accompanying claims includes, but is not limited to rubber, silicone, PVC, Tygon™ and other soft plastics. According to still further features in the described preferred embodiments the at least one of the at least one support member is a bifurcated support member.

According to still further features in the described preferred embodiments an external source of positive pressure is further included. Preferably, the external source of positive pressure includes a pump capable of causing at least one gas to flow through a connecting conduit, the connecting conduit reversibly engageable by the gas exchange port.

According to still further features in the described preferred embodiments the present invention constitutes a treatment modality for a disorder selected from the group consisting of obstructive sleep apnea (OSA), apnea of infancy (AOI), sudden infant death syndrome (SIDS) and snoring.

The present invention successfully addresses the shortcomings of the presently known configurations by providing a device for preventing collapse of the upper airway in a human subject. Further the present invention successfully addresses the shortcomings of the presently known configurations by providing an improved pacifier and method of use thereof which facilitate mouth breathing while preventing collapse of the upper airway in infants and young children. According to many embodiments, the present invention does not require the use of CPAP technology and provides a safe alternative to surgical intervention. User compliance is greatly improved.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 5 is a frontal view of the operative portion of a mechanism capable of transforming kinetic energy of air flowing in a first direction to potential energy and further transforming said potential energy to kinetic energy of air flowing in a second direction according to the present invention.

FIG. 6 is a lateral cross section of the mechanism illustrated in FIG. 5 installed as part of a system for prophylactic treatment of a breathing disorder according to the present invention in a first operational state.

FIG. 7 is a similar view of the system of FIG. 6 illustrating a second operational state thereof.

FIG. 8 depicts a system according to FIGS. 6 and 7 in use.

FIGS. 9a, 9b, 12a, 12b, 13a and 13b are cross sectional views of various embodiments of an improved pacifier according to the present invention.

FIGS. 10a and 10b are cross sectional views as in 1a and 1b showing how the improved pacifier is switched from one operational state to another during sucking.

FIGS. 14, 15, 16 are perspective views of devices according to the present invention.

FIG. 17 is a simplified flow diagram illustrating sequences of events associated with performance of methods according to the present invention.

DESCRIPTION OF THE PREFERRED EMBODIMENTS

Figure 1:
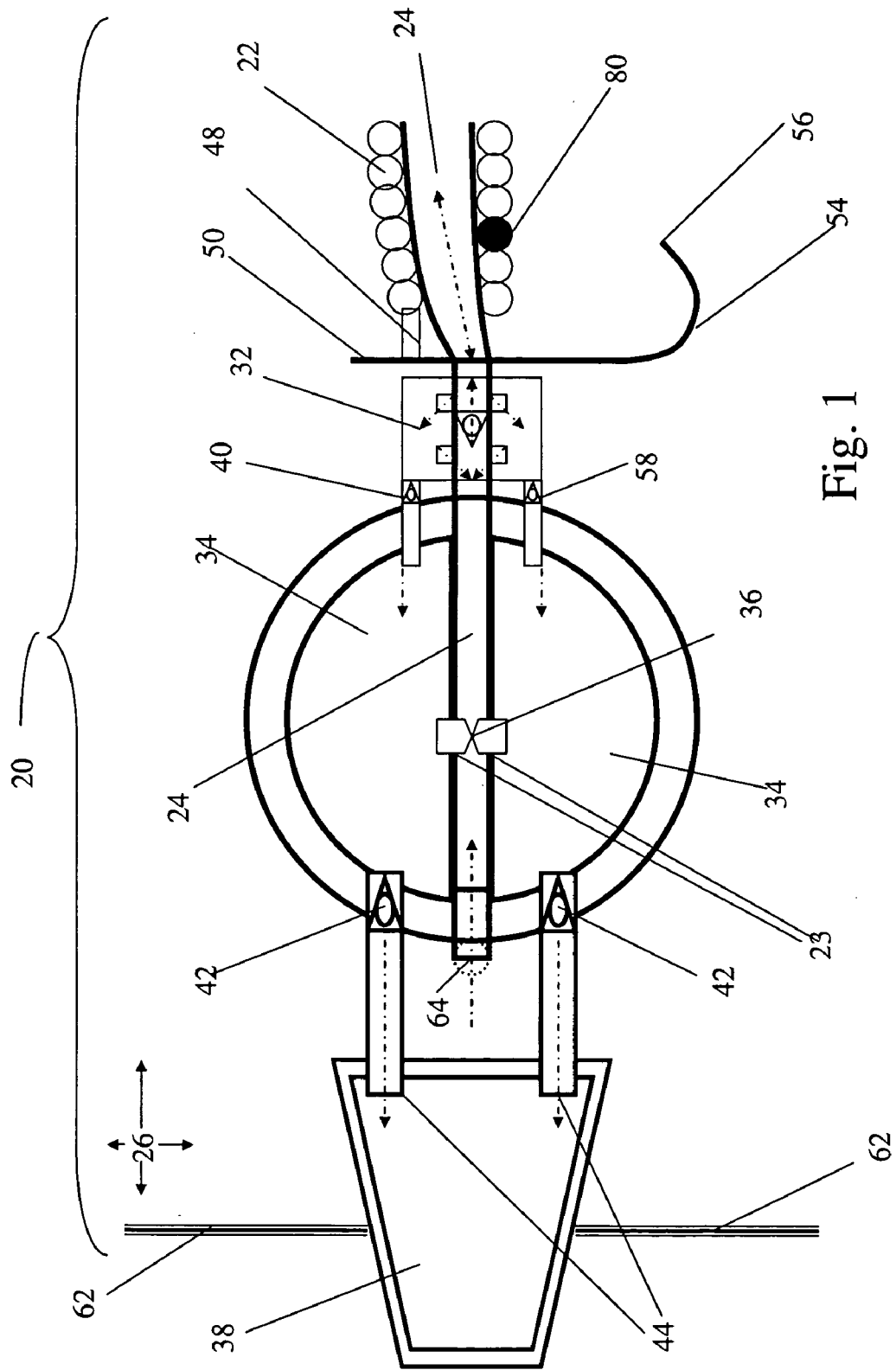
FIG. 1 is a schematic representation of a device according to the present invention.

The present invention is of devices for preventing collapse of the upper airway, methods for use thereof and systems and articles of manufacture including same. The present invention is further of devices, systems and methods which monitor parameters of air exhaled by a patient through such a device and of a physiologic status of a patient breathing through such a device. Devices of the present invention may, in some cases, take the form of a pacifier.

Specifically, the present invention can be used to prevent or treat a variety of conditions including, but not limited to, obstructive sleep apnea (OSA), apnea of infancy (AOI) and sudden infant death syndrome (SIDS) and to improve patient compliance with recommended treatment protocols.

The principles and operation of a self contained constant pressure applied proximally (CPAP) device and of systems and methods which prevent collapse of the upper airway according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
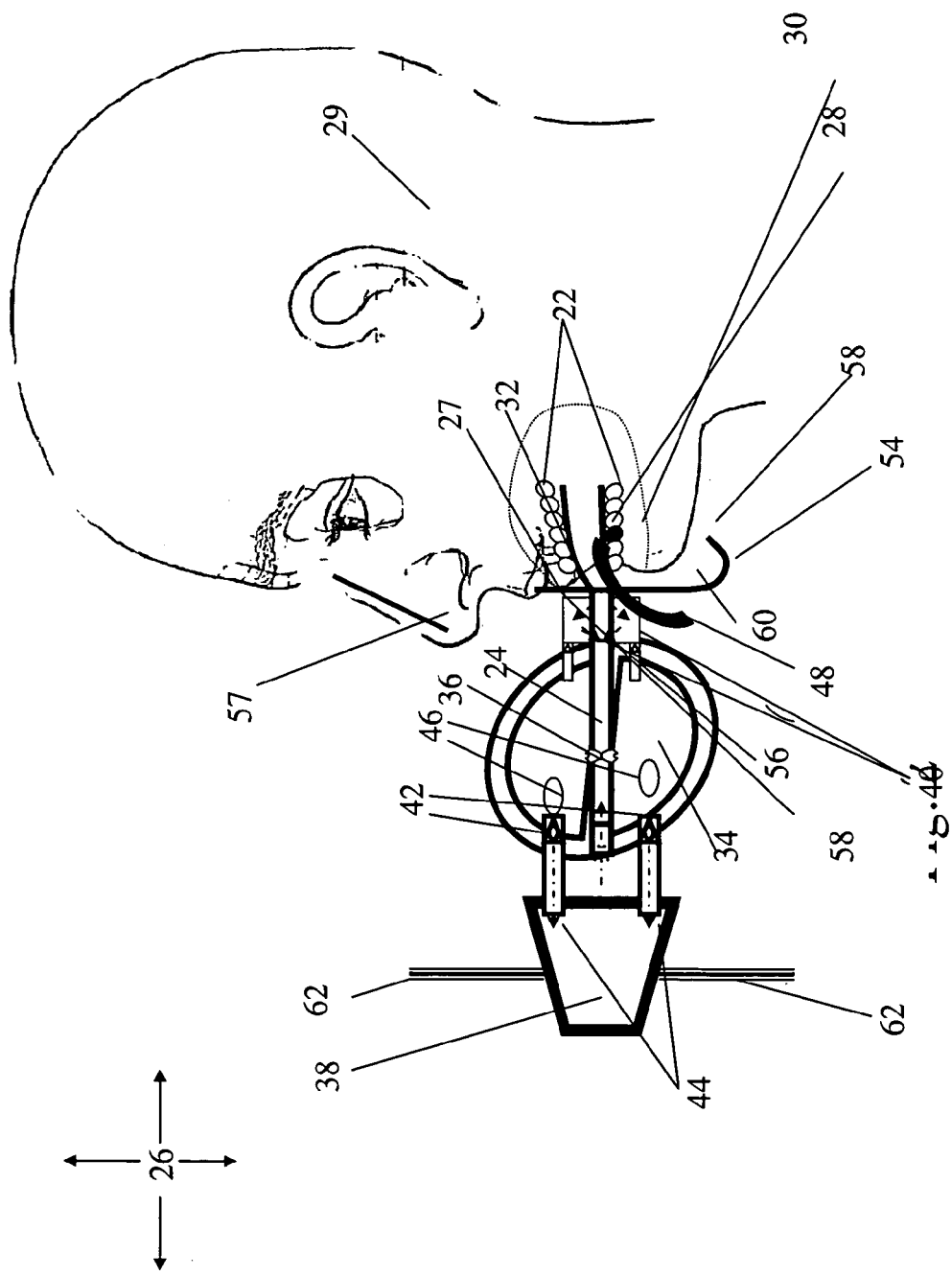
FIG. 2 depicts insertion of the device of FIG. 1 into a mouth of a patient.

Referring now to the drawings, FIG. 1 illustrates the self contained CPAP device 20 of the present invention. Device 20 includes a mouthpiece 22 insertable in a mouth 28 (FIG. 2) of a patient. Mouthpiece 22 may be adjustable to fit the interior 30 of mouth 28 of the patient. According to some preferred embodiments of the present invention, a mechanism for facilitating inflation 48 of mouthpiece 22 is provided. According to preferred embodiments of the present invention there is provided a mechanism for sealing 50 between mouthpiece 22 and lips 27 of the patient, such that airflow between lips 27 and mouthpiece 22 is diminished.

According to preferred embodiments of the present invention device further includes a chin holder 54 having a first end 56 which is capable of engaging a chin 60 of the patient and a second end 58 which is connectable to the device.

Device 20 also includes a breathing tube 24 connecting between an outside environment 26 and an interior 30 of mouth 28. Breathing tube 24 contains at least one bidirectional pressure sensitive valve 32. Valve 32 serves to allow inhalation of air via tube 24 during inhalation, and to allow expiration of air during exhalation. Tube 24 has an internal cross sectional area 36 which changes during respiration as will be described hereinbelow. In the pictured embodiment of device 20, tube 24 has holes 23 therein.

In the pictured preferred embodiment breathing tube 24 passes through the mouthpiece to outside environment 26, although tube 24 could pass, for example between mouthpiece 22 and lips 27 without substantially effecting the function of device 20. In the pictured preferred embodiment (FIGS. 1, 2, and 3) tube 24 further includes a filter 25 designed and constructed to prevent the entry of foreign bodies thereto.

Device 20 also includes at least one inflatable body 34 which functions to adjust internal cross sectional area 36 of breathing tube 24 during a process of respiration. Inflatable body 34 further serves to regulate an air pressure within mouth 28 during the process of respiration. The process by which this regulation occurs is detailed hereinbelow. Inflatable body 34 includes at least one elastic balloon (also labeled 34), at least one first additional unidirectional pressure sensitive valve 40 in communication an interior of breathing tube 24 and at least one second additional unidirectional pressure sensitive valve 42 in communication with an re-inhaled air tube 44. Re-inhaled air tube 44 is in communication with a mask 38. This configuration assures that exhaled air passes through pressure sensitive valve 40, thereby inflating inflatable body 34 and causing an elevated pressure to form therein and that reduction of the elevated pressure is accomplished by a release of exhaled air through pressure sensitive valve 42 into re-inhaled air tube 44 which directs the re-inhaled air to mask 38.

Inflatable body 34 may include any number of inflatable bodies (two are pictured in the drawings) having a total inflated volume which is approximately 2 to 4 ml greater than a total deflated volume thereof for each Kg of mass of said patient. For example, inflatable body 34 might have a total inflated volume which is approximately 120 to 350 ml greater than a total deflated volume thereof such that it is suitable for use in adults, or it might have a total inflated volume which is approximately 40 to 160 ml greater than a total deflated volume thereof such that it is suitable for use in children, or it might have a total inflated volume which is approximately 2 to 40 ml greater than a total deflated volume thereof such that it is suitable for use in infants.

According to some preferred embodiments of device 20, inflatable body 34 further comprises at least one unidirectional pressure sensitive safety valve 46 in communication with the outside environment 26. Safety valve 46 functions to prevent explosion of inflatable body 34 by opening to release air to outside environment 26. Safety valve 46 opens when a predetermined inflated volume is exceeded. Since inflatable body 34 will have an elevated pressure as a volume thereof increases, safety valve 46 can also be said to release exhaled air when the elevated pressure exceeds a predefined limit.

Device 20 also includes mask 38 in fluid communication with inflatable body 34 by means of re inhaled air tube 44. Mask 38 is designed and constructed to cover a nose 57 of the patient, such that exhaled air is routed thereto. One ordinarily skilled in the art will be capable of modifying a commercially available mask for use with the present invention. Masks are available from, for example, www.respironics.co; www.sleep-net.com; and www.sunrisemedicalonline.com.

The present invention is further embodied by a system for prophylactic treatment of a breathing disorder. The system includes a self contained CPAP device which is designed and constructed to maintain sufficient pressure in an upper airway of a patient such that collapse thereof is prevented. Self contained CPAP device functions independently of, for example, a pump, a compressor, a pressurized gas cylinder and an electro-hydrolytic oxygen source.

The present invention is further embodied by an improved method of preventing a breathing disorder by means of CPAP. The method includes at least four steps. The first step includes inserting mouthpiece 22 in mouth 28 of a patient. The second step includes allowing inhaled air to flow through at least one bi-directional pressure sensitive valve 32 contained within breathing tube 24 which connects outside environment 26 and an interior 30 of mouth 28. The third step includes adjusting internal cross sectional area 36 of breathing tube 24 during a process of respiration by means of at least one inflatable body 34 which serves to regulate an air pressure within mouth 28 during the process of respiration. The fourth step includes covering nose 57 of the patient with mask 38 which is in fluid communication with inflatable body 34 and is designed and constructed to receive exhaled air therefrom and route the exhaled air to nose 57 of the patient. The method may sometimes include the additional step of adjusting mouthpiece 22 to fit mouth 28 of the patient. This additional step may be accomplished by, for example, inflating mouthpiece 22.

According to some preferred embodiments of the present invention, device 20 further comprises at least one retaining piece 62 for holding the device in place. Retaining piece 62 may include, for example, at least one strap, at least one elastic band, at least one piece of Velcro™ or a pair of protrusions which engage the ears 59 of the patient.

Device 20 may be specifically designed and configured for many purposes including, but not limited to, treating obstructive sleep apnea, treating apnea of infancy and preventing sudden infant death syndrome.

Figure 3:
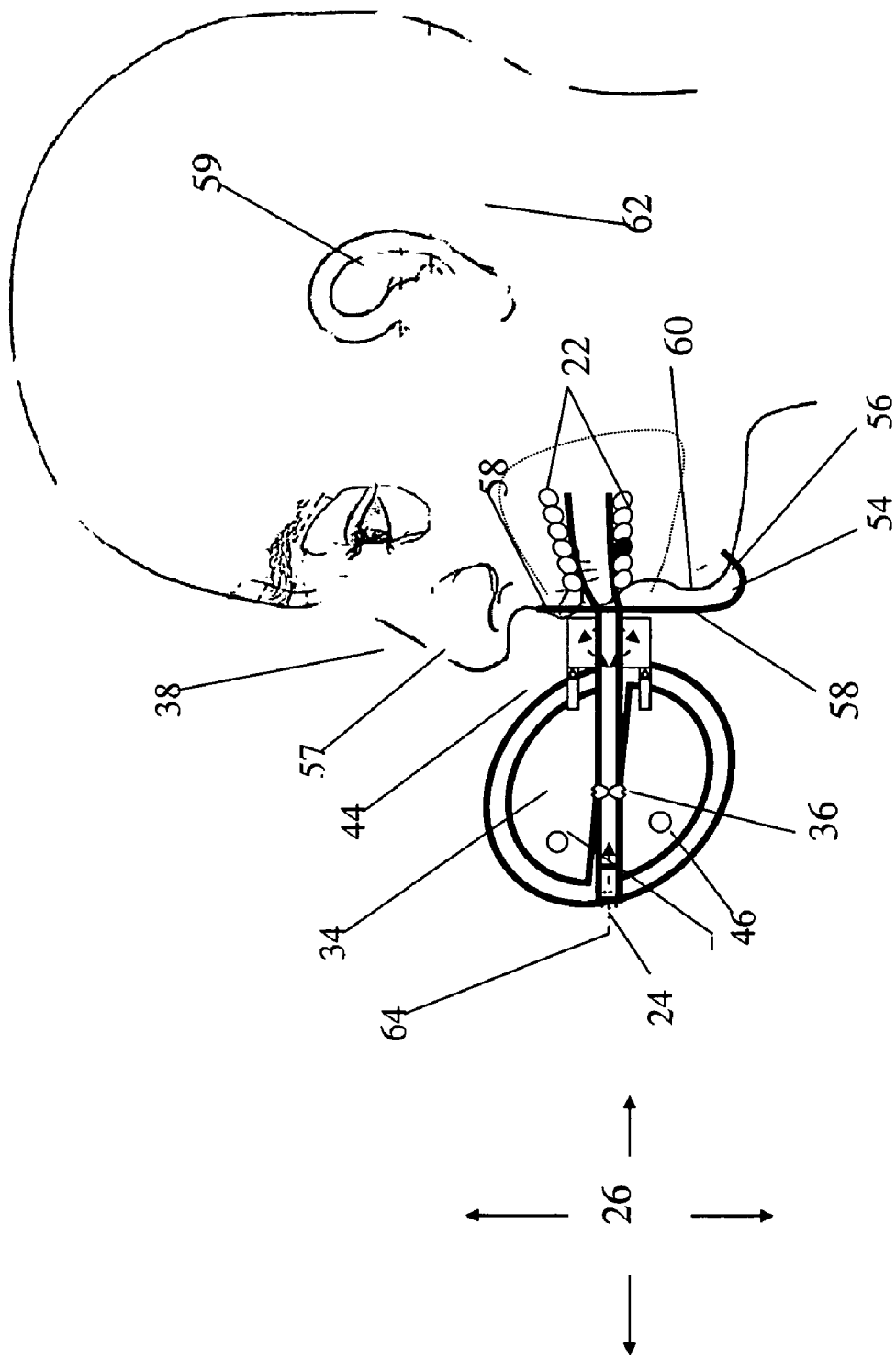
FIG. 3 depicts a device according to the present invention as in FIG. 2 with the mask covering the nose of a patient.

Having set forth the component parts of device 20, an explanation of their integrated function during respiration will now be provided. FIG. 4a shows the flow of air (arrows) from outside environment 26 via breathing tube 24 with internal cross sectional area 36 into interior of the mouth 30 during the first inhalation of a patient that has assembled device 20 on their face (as shown in FIG. 3). Flow of air through valve 32 is inward towards mouthpiece 22. Valve 32 opens at a very low pressure in this direction, for example 1 cm of $H_2O$ or less. There is no flow of air at this stage through valves 40 and 42. Inflatable bodies 34 do not protrude through holes 23 because they are not yet inflated.

Figure 4B:
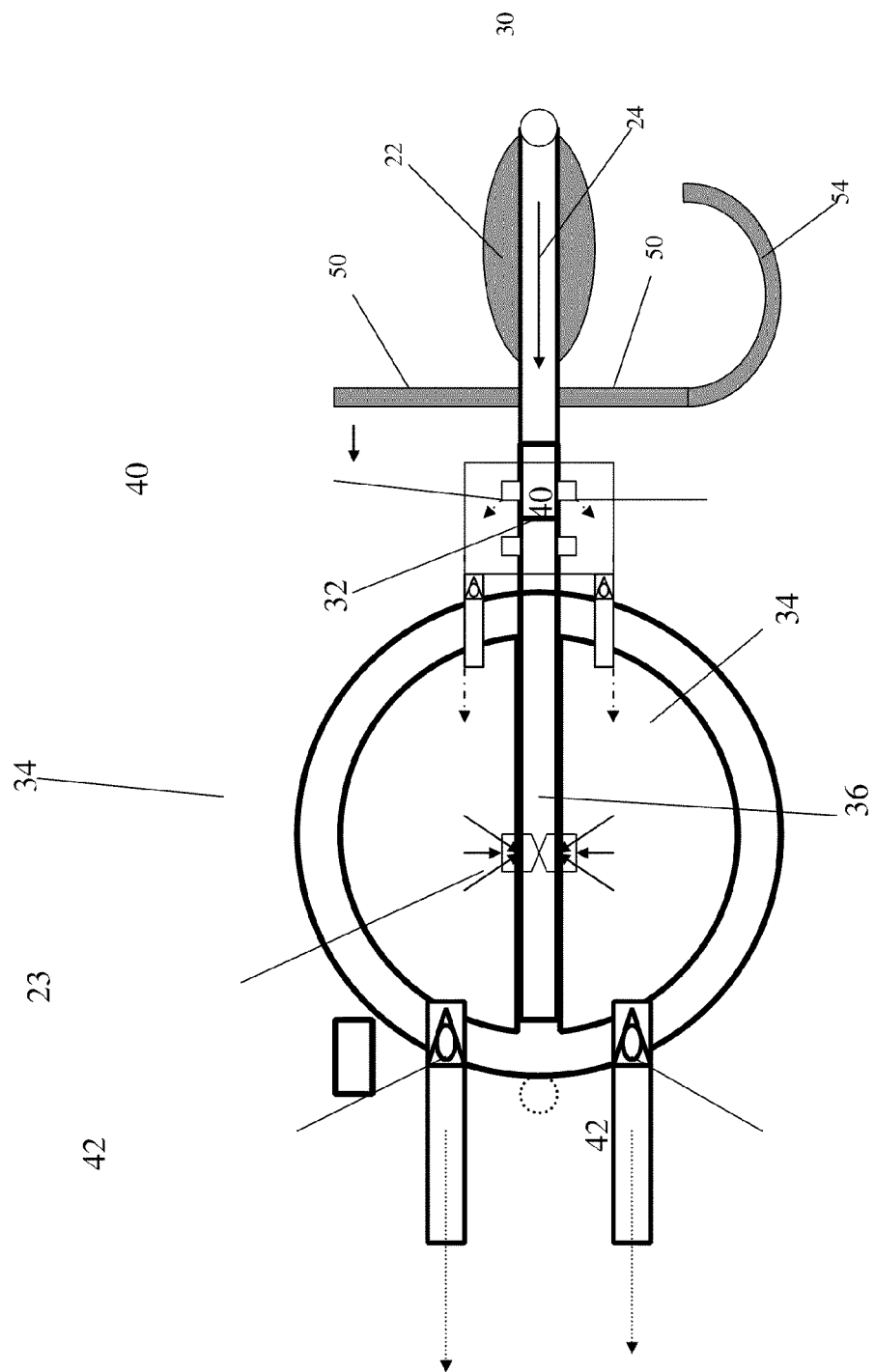
FIGS. 4a, b, and c illustrate airflow through a device according to the present invention during an initial inspiration, an exhalation and all subsequent inhalations respectively.

FIG. 4b shows the flow of air (arrows) during exhalation. Airflows outward from interior of mouth 30 via breathing tube 24 towards unidirectional valves 40 and bi-directional valve 32. Valves 40 open at a lower pressure than valve 32 so that exhaled airflows primarily into inflatable body 34 which begins to protrude through holes 23 in tube 24 as it expands, thereby reducing cross sectional area 36 of tube 24. Reduction of cross sectional area 36 of tube 24 is significant, for example reduced area 36 may be as little as one quarter or one eighth of initial area 36. As pressure within inflatable body 34 increases, valves 42, which communicate with re-inhaled air tube 44 (FIGS. 1, 2, and 3) open. This establishes a flow of air under slight positive pressure through nose 57 into interior of mouth 30 and subglottal region 29 of the airway. The positive pressure is preferably in excess of 12 cm of water, more preferably between 12 and 40 cm of water and most preferably approximately exactly 40 cm of water. This pressure also causes inflatable body 34 to expand through holes 23 in tube 24 thereby reducing cross sectional area 36 thereof. Approximately 300 ml of pressurized exhaled air collects in inflatable body 34 during exhalation. Because inflatable body 34 is elastic, this air continues to flow outward through valves 42 after exhalation ceases. Because valves 40 are unidirectional, air does not flow back into tube 24 from inflatable body 34. During exhalation, outward airflow through bi-directional valve 32 is partially obstructed because inflatable body 34 reduces cross sectional area 36 of tube 24 significantly as explained hereinabove. Inflatable body 34 also compresses partially elastic bi-directional valve 32 in order to allow some exhaled air to flow through tube 24 to outside environment 26.

Figure 4C:
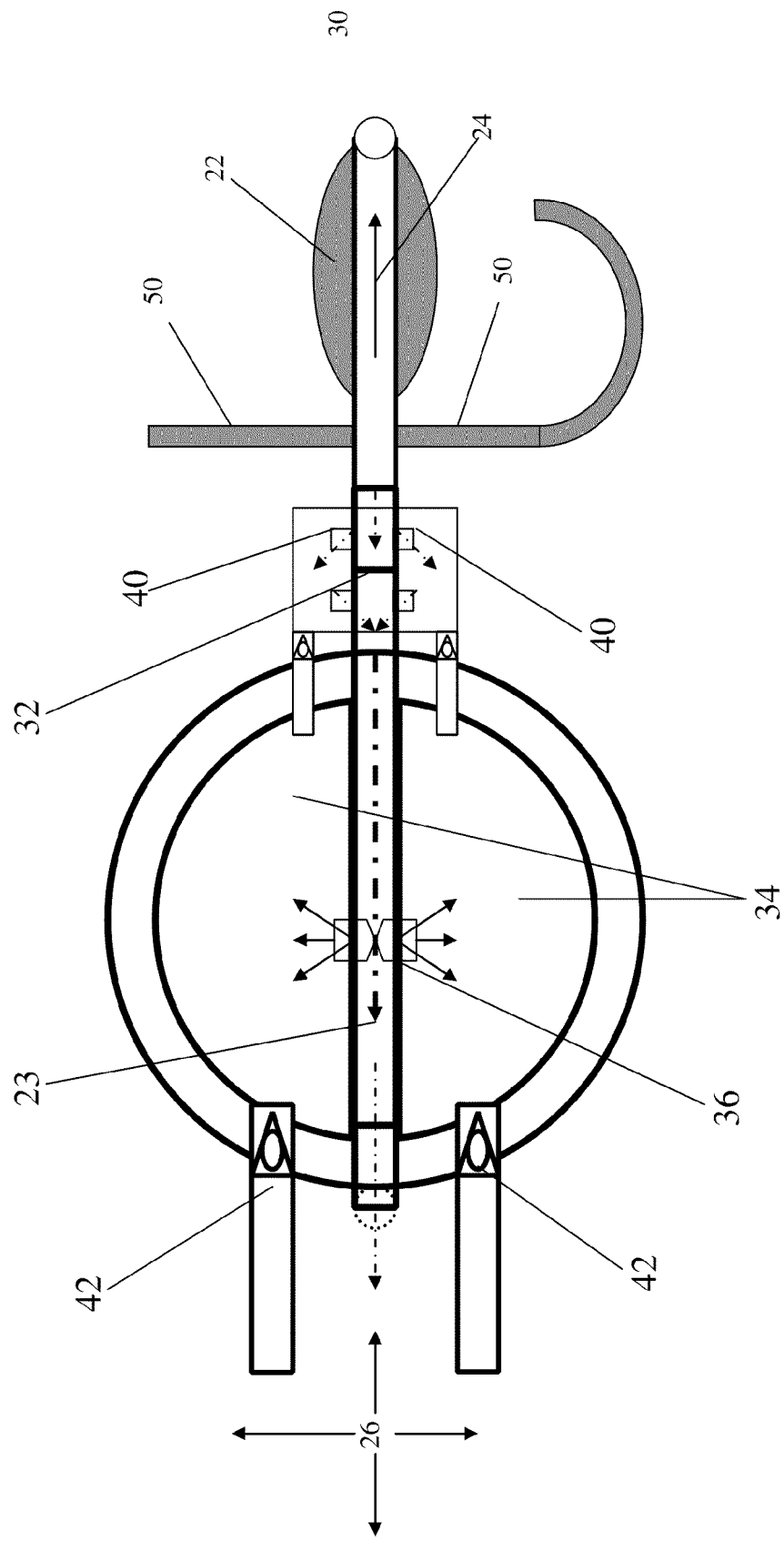
Figure 11:
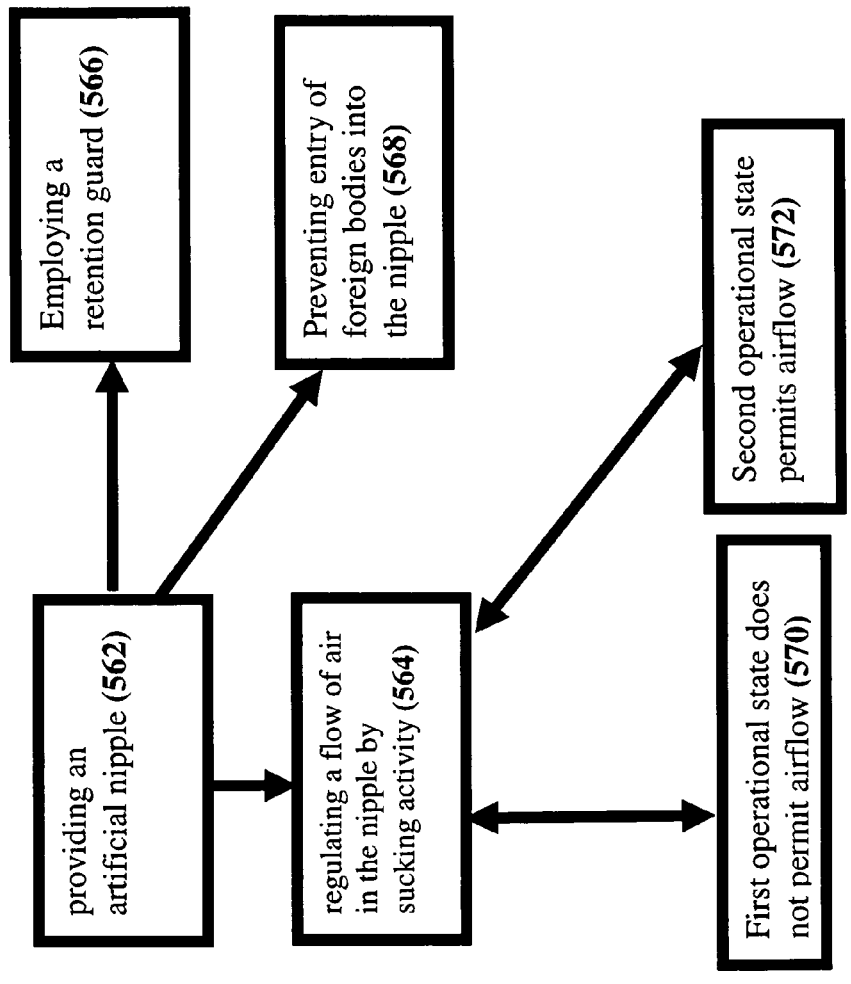
FIG. 11 is a simplified flow diagram of a method according to the present invention.

During subsequent inhalations (FIG. 4c), air continues to flow outward through valves 42 maintaining positive pressure in the subglottal region 29 of the upper airway as described hereinabove. This outward flow reduces the volume of inflatable body 34 which tends to withdraw from holes 23 in tube 24 thereby increasing cross sectional area 36. Airflow during subsequent inhalations is otherwise as described for the first inhalation hereinabove.

Function of device 20 as described hereinabove is dependent to a large degree upon pressure differentials for operation of valves 32 and 40 and for operation of valves 40 and 42. In general, a pressure difference of 1 cm of water for each of these pairs should be sufficient to facilitate operation of device 20. One ordinarily skilled in the art will be able to assemble device 20 using commercially available valves from, for example, Hans Rudolph Inc. (Kansas City, Mo., USA). Valves 42 may be, in some preferred embodiments, two stage valves, such that inhalation via nose 57 is required to initiate release of exhaled air from inflatable body 34 via valves 42.

A simplified, and perhaps most preferred, embodiment of the present invention is a device 20 (FIGS. 1 and 8) for preventing collapse of the upper airway which includes a mouthpiece 22 insertable in mouth 28 of a patient and a breathing tube 24 connecting between an outside environment 26 and interior 30 of mouth 28. Preferably, mouthpiece 22 is adjustable to fit mouth 22 of the patient, for example by mechanism for inflating 48 (FIG. 1). As described hereinabove, breathing tube 24 preferably passes through mouthpiece 22. Preferably device 20 further includes a filter 25 designed and constructed to prevent the entry of foreign bodies into breathing tube 24 thereto. According to some preferred embodiments of the present invention device 20 further includes a humidifying element 31 designed and constructed to add moisture to inhaled air. Humidifying element 31 serves to prevent tissues dehydration in the mouth and airway. Preferably, filter 25 and humidifying element 31 are physically incorporated into a single unit as illustrated in FIG. 8. According to additional preferred embodiments of the present invention, device 20 further includes a sensor 80 in breathing tube 24. Sensor 80 is designed and constructed to measure a parameter such as, for example, an air parameter or a patient parameter. The air parameter may be, for example, air velocity, air volume or relative humidity. The patient parameter may be, for example, O2 saturation of the patient, a body temperature of the patient or a partial pressure of a gas in exhaled air. Partial pressure of a gas such as $CO_2$, $O_2$, CO or NO is specifically included in the definition of patient parameter, although partial pressures of other gases may be measured if they are deemed medically relevant. Air flow and air volume may be measured, for example, by a portable spirometer such as the Zephyr PC (Advanced Biosensor, Colombia South Carolina) or another commercially available device.

Partial pressure of a gas may be measured, for example, using a miniaturized pulse oximeter such as those manufactured by Palco and Nonin and distributed by Aeromedix.com.

One of ordinary skill in the art of engineering will be able to incorporate a commercially available sensor into the context of the present invention. Sensor 80 is equipped with a display device 37 which registers data of the sensed parameter. Display 37 may be physically connected to device 20 or situated at a remote location, for example a nursing station. A channel of communication 33 facilitates transfer of data between sensor 80 and display 37. For purposes of this specification and the accompanying claims, the phrase "channel of communication" refers to a telephone connection, a cellular telephone connection, an Internet connection, an infrared frequency transmission connection, a local area network connection, a radio frequency connection, a fiber-optic connection or a connection by a wire. Inherent in the idea of a communication channel is an open status during which data transmission may occur. In some cases, communication channels may also have a closed status during which no data transmission may occur. Thus, according to some embodiments of the invention, patient 120 will monitor data displayed on display 37, which may be, for example, mounted on a wrist band, pocket or belt. According to other preferred embodiments of the invention, medical personnel will monitor data displayed on display 37. This monitoring may be local, for example by a personal nurse, or remote by means of established telemedicine techniques. Thus monitoring of data on display 37 may be constant, intermittent or periodic and may occur in real time or with a delay. Data processing capability is inherent in either sensor 80 or display 37 which may be, for example, the display of a personal computer.

Thus, the present invention is further embodied by a method of preventing collapse of the upper airway. The method includes inserting a mouthpiece 22 in a mouth of a patient and allowing inhaled air to flow through a breathing tube 24 connecting between an outside environment 26 and an interior 30 of mouth 28. This method includes all of the variations described hereinabove for device 20.

The present invention further provides a system for prophylactic treatment of a breathing disorder. The system includes a self contained CPAP device. The device 20 is designed and constructed to maintain sufficient pressure in an upper airway of a patient 120 such that collapse thereof is prevented. The system of the present invention functions without a pump, a compressor, a pressurized gas cylinder or an electro-hydrolytic oxygen source. The system includes mouthpiece 22 insertable in a mouth 28 of patient 120. The system further includes breathing tube 24 connecting between outside environment 26 and interior 30 of mouth 28. Breathing tube 24 contains at least one bi-directional pressure sensitive valve 32 therein or a pair of opposing unidirectional ports 103 and 104 which function together as a bidirectional pressure sensitive valve. The system further includes a mechanism capable of transforming kinetic energy of air flowing in a first direction to potential energy and further transforming the potential energy to kinetic energy of air flowing in a second direction. The mechanism capable of transforming kinetic energy of air flowing in a first direction to potential energy and further transforming the potential energy to kinetic energy of air flowing in a second direction may include, but is not limited to, an inflatable body 34 as described hereinabove or a turbine 100 as described hereinbelow. Preferably, the system further includes a mask 38 in fluid communication with the mechanism (e.g. 34 or 100) capable of transforming kinetic energy of air flowing in a first direction to potential energy and being designed and constructed to cover a nose 57 of patient 120, such that exhaled air is routed thereto. According to some preferred embodiments of the invention mouthpiece 22 and lips of patient 120 are sealed by mechanism for sealing 50 so that airflow between the lips and mouthpiece 22 is diminished.

It is often advantageous to incorporate a chin holder 54 having a first end which is capable of engaging a chin 60 of patient 120 and a second end which is connectable to device 20 so that device 20 is held firmly in place during use.

In most, but not all, configurations of device 20, breathing tube 24 passes through mouthpiece 22, although this is not essential to function of the system. As described hereinabove, device 20 is often constructed with at least one retaining piece. Preferably, device 20 further includes a filter 25 in breathing tube 24 as described hereinabove. Optionally, a humidifying element 31 may be included as described hereinabove.

The present invention is further embodied by an improved method of preventing a breathing disorder by means of CPAP. The method includes inserting mouthpiece 22 in mouth 28 of patient 120 and allowing inhaled air to flow through at least one bi-directional pressure sensitive valve 32 contained within breathing tube 24 connecting between outside environment 26 and an interior 30 of mouth 28. Valve 32 may be, for example, a pair of opposing unidirectional ports 103 and 104 which function together as a bi-directional pressure sensitive valve. The method further includes providing a mechanism (e.g. 34 or 100) capable of transforming kinetic energy of exhaled air flowing in a first direction to potential energy and further transforming the potential energy to kinetic energy of air flowing in a second direction into a proximal airway of the patient thereby regulating an air pressure within the mouth during the process of respiration. Preferably, the method further includes covering nose 57 of patient 120 with a mask 38 in fluid communication with the mechanism (e.g. 34 or 100) capable of transforming kinetic energy of exhaled air as described hereinabove.

According to yet another additional aspect of the present invention there is provided a system for prophylactic treatment of a breathing disorder including a self contained CPAP device 20 as described hereinabove and further including a sensor 80 designed and constructed to measure at least one parameter as described hereinabove. Sensor 80 may reside, for example, at a location selected from breathing tube 24 and inflatable body 34.

Workings of a mechanism capable of transforming kinetic energy of exhaled air in the form of inflatable body 34 have been described in detail hereinabove. Referring now to FIG. 5, an additional non-limiting example of such a mechanism will be provided. Turbine 100 which is capable of rotational motion in two directions (arrows) about an axis 101 is attached to energy storage component 102. The term turbine, as used herein, includes all configurations of airscrews, propellers or vanes which are capable of performing the function described herein. Energy storage component 102 may be, for example a coiled spring or elastic band. Exhaled air 105 (FIG. 6) flows outward via breathing tube 24 causing turbine 100 to rotate about axis 101 in a first direction thereby storing kinetic energy from exhaled air 105 as potential energy in energy storage component 102. Pressure sensitive unidirectional ports 103 and 104 function together as bi-directional pressure sensitive valve 32 in the pictured embodiment. This is preferable because it insures that some fresh air enters the system with each inhalation. Exhaled air 105 flows to outside environment 26 via ports 103. Port 104 remains closed in this operational state of device 20.

Inhalation (FIG. 7) occurs during a second operational state of device 20. Fresh air 106 flows inward via breathing tube 24 after entering via port 104. Concurrently, turbine 100 rotates about axis 101 in a second direction, activated by the release of stored potential energy from energy storage component 102. This pushes additional fresh air 106 from outside environment 26 into the airway of patient 120. Ports 103 remains closed in this operational state of device 20.

FIG. 8 depicts a device according to the present invention in use by a patient 120.

The present invention may be embodied as an improved pacifier which can be advantageously employed to facilitate mouth breathing while preventing collapse of the upper airway in infants and young children. Specifically, the improved pacifier can be used to treat breathing disorders including, but not limited to, apnea of infancy (AOI), sudden infant death syndrome (SIDS) and Rhinitis. Treatment, as used herein, is typically palliative or prophylactic treatment. Because the present invention is both safe and non-invasive, it may be used by either identified high-risk patients or by the general population of children that use conventional pacifiers.

The principles and operation of an improved pacifier according to the present invention may be better understood with reference to the drawings and accompanying descriptions.

Referring again to the drawings, FIGS. 9a, 9b, 10a, 10b 12a, 12b, 13a and 13 illustrate the improved pacifier 520 of the present invention either alone (FIGS. 9a, 9b, 12a, 12b, 13a and 13) or in the context of a mouth of a patient engaged in sucking activity (FIGS. 10a and 10b). Pacifier 520 includes an artificial nipple 522 designed and constructed to stimulate sucking when inserted in a mouth 550 of a young patient. Nipple 522 is typically constructed of a soft plastic, rubber or silicon material as generally employed in conventional pacifiers although other materials may be employed without significantly affecting the functionality of the pacifier. Nipple 522 includes a proximal portion 526 insertable in mouth 550 of the patient. Nipple 522 further includes a distal portion 524 which protrudes from mouth 550 during use. Nipple 522 is hollow and includes an interior volume 528 which serves as a first channel 534 of fluid communication between at least one first aperture 532 and at least one second aperture 530. Second aperture 530 located in distal portion 524 of nipple 522 forms a second channel 536 of fluid communication between interior volume 528 of artificial nipple 522 and an external environment. First aperture 532 forms third channel 538 of fluid communication between the interior volume 528 of artificial nipple 522 and mouth 550. Pacifier 520 further includes an air flow valve 540 having a first operational state 544 (FIGS. 9b, 10b, 12b and 13b) in which the first channel 530 of fluid communication is closed and a second operational state 542 (FIGS. 9a, 10a, 12a and 13a) in which the first channel 534 of fluid communication is open. Pacifier 520 is constructed so that extension of tongue 554 in an upward direction against nipple 522 during sucking causes air flow valve 540 to assume first operational state 544. Subsequent cessation of sucking allows the air flow valve 540 to assume second operational state 542 as tongue 554 moves downward from nipple 522.

Pacifier 520 preferably further includes a retention guard 546 designed and constructed to prevent swallowing of artificial nipple 522. Retention guard 546 may be, for example, attached to or integrally formed with the distal portion 524 of artificial nipple 522 so that it naturally resides outside of lips 552 during use. Pacifier 520 may further include a filter 548 designed and constructed to prevent the entry of foreign bodies thereto. Filter 548 may be located, for example, in proximity to second aperture 530.

It will be appreciated that different configurations of valve 540 give rise to different embodiments of the claimed invention. Several such configurations are offered as non-limiting examples.

FIGS. 9a, 9b, 10a and 10b illustrate a valve 540 including a lever 539 connected via an axle 541 to a flap 541. Pressure of tongue 554 on nipple 522 raises lever 539 causing axle 541, mounted on a surface of interior volume 528 of nipple 522 to rotate thereby causing flap 541 to close second aperture 530. A similar valve could be employed to close first aperture 532 without significantly changing the function of the invention.

FIGS. 12a and 12b illustrate a valve 540 including two flexible leaves 545. Pressure of tongue 554 on nipple 522 causes leaves 545 to come into contact one with the other thereby closing first channel 534.

Figure 13A:
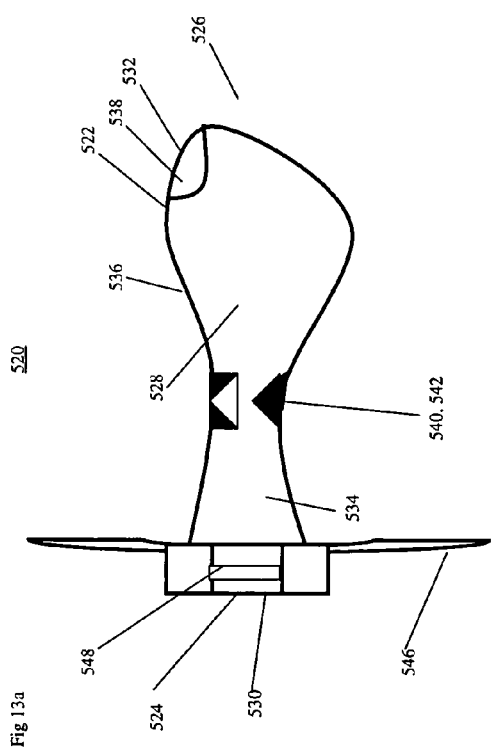
Figure 13B:
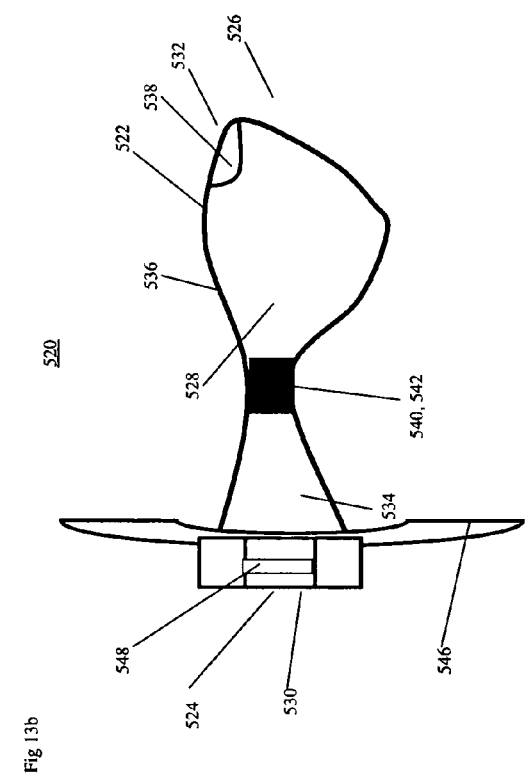
Figure 18:
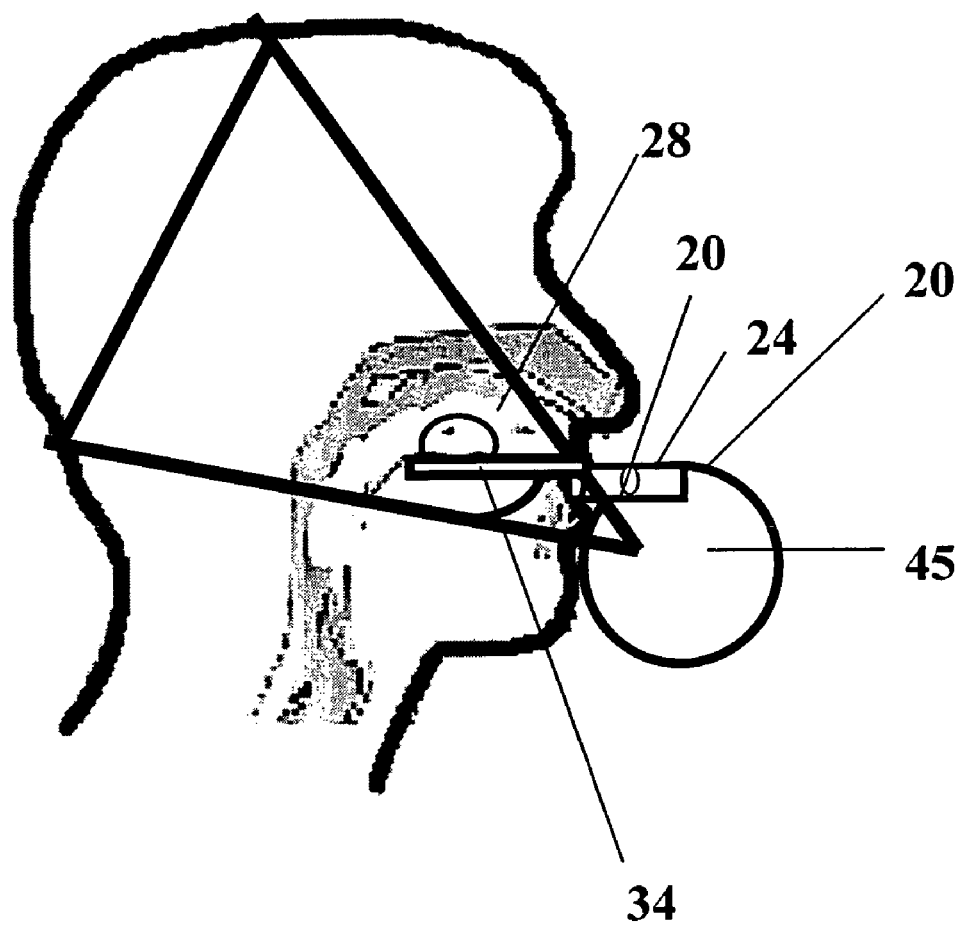
FIG. 18 is a lateral cross sectional views of a device according to the present invention in use.

FIGS. 13a and 13b illustrate a valve 540 including a convex portion 549 and a concave portion 549. Pressure of tongue 554 on nipple 522 causes convex portion 549 to come into contact with concave portion 549 thereby closing first channel 534.

Leaves 545 and convex portion 549 and concave portion 549 may be integrally formed with or attached to a surface of interior volume 528 of nipple 522. These parts of valve 540 may be constructed, for example, of the same rubber or silicon used to construct nipple 522.

The present invention is further embodied by a method 560 of facilitating mouth breathing in a young patient. Method 560 includes providing 562 artificial nipple 522 designed and constructed to stimulate sucking when inserted in mouth 550 of the young patient. Nipple 522 has a proximal portion 526 insertable in mouth 550 and a distal portion 524 protruding therefrom. Nipple 522 is hollow and includes an interior volume 528 with first aperture 532 and second aperture 530 connected by channel of fluid communication 534 as described hereinabove. Method 560 further includes regulating 564 a flow of air in channel of fluid communication 534 by means of air flow valve 540. As described hereinabove, valve 540 has a first operational state 544 in which channel of fluid communication 534 is closed and second operational state 542 in which channel of fluid communication 534 is open.

As described hereinabove sucking 570 causes air flow valve 540 to assume first operational 544 state while cessation 572 of sucking allows the air flow valve to assume the second operational state. Thus, it will be appreciated that the phrase "young patient", as used herein and in the accompanying claims, refers to a patient that habitually uses a pacifier as a means of relaxation. This habitual pacifier use may occur, for example, during sleep.

Preferably, method 560 further includes employing 566 retention guard 546 designed and constructed to prevent swallowing of artificial nipple 522. Retention guard 546 may be, for example, attached to or integrally formed with distal portion 524 of artificial nipple 522.

Optionally, but also preferably, method 560 further includes preventing 568 the entry of foreign bodies into channel 536 or 534 of fluid communication by means of a filter located in proximity to second aperture 530.

In summary, improved pacifier 520 of the present invention allows air to enter mouth 550 via interior volume 528 of nipple 522 and be directed to airway 556 during inspiration. Pacifier 520 further serves to prevent entry of air into esophagus 555 during sucking. This unique action both helps to establish oral access to the airway to facilitate mouth breathing and reduces frustration of a user with an occluded nasal passage. Thus a primary benefit of the invention is a prophylactic or palliative treatment for disorders such as AOI or SIDS while a secondary benefit of the invention is a reduction in frequency of waking for young patients with an occluded nasal passage.

Referring again to the drawings, FIG. 14 illustrates an especially preferred device 20 for preventing collapse of the upper airway in a human subject according to the present invention. Device 20 includes mouthpiece 22 insertable in mouth 28 of a human subject. Device 20 further includes an inflatable positioning aid 34 adjustable to fit the mouth by inflation. Inflation is preferably accomplished by means of a gas exchange port 19 providing a regulatable channel of fluid communication between inflatable positioning aid 34 and an external source of positive pressure. Positioning aid 34 may be attached to or integrally constructed with mouthpiece 22. Inflation of positioning aid 34 causes an asymmetric protrusion 21 (see FIG. 16) of the positioning aid from mouthpiece 22. Device 20 further includes a breathing tube 24 connecting between an outside environment 26 and an interior 30 of mouth 28. Furthermore, the mouthpiece also has an upper surface and a lower surface that are substantially parallel to a plane defined by the breathing tube 24. When used, the device prevents collapse of the upper airway of the human subject. The phrase "outside environment" as used in this specification and the accompanying claims refers to ambient air and specifically excludes any gas contained within a pressurized canister, balloon, bag or other delivery device.

Asymmetric protrusion 21 is preferably above breathing tube 24 so that positioning aid 34 fits into the roof of the mouth. Preferably, tongue movement is at least partially restricted.

According to another aspect of the present invention there is provided a method 70 (FIG. 17) of preventing collapse of the upper airway in a human subject. The method includes inserting 72 mouthpiece 22 in mouth 28 of the human subject. Method 70 further includes inflating 74 inflatable positioning aid 34 essentially as described hereinabove. Positioning aid 34 causes mouthpiece 34 to be engaged and retained in a desired position in interior 30 of mouth 28 by means of asymmetric protrusion 21 of positioning aid 34 from mouthpiece 22. Method 70 further includes allowing 76 inhaled air to flow through a breathing tube connecting between an outside environment and an interior of the mouth so that collapse of the upper airway of the human subject is prevented 82.

According to yet another aspect of the present invention there is provided an article of manufacture. The article of manufacture includes: (a) a device for preventing collapse of the upper airway in a human subject essentially as described hereinabove and hereinbelow; (b) packaging material; and (c) instructions for use identifying the device as efficacious in preventing collapse of the upper airway of the human subject.

Optionally, but preferably, breathing tube 24 passes through mouthpiece 22. According to some preferred embodiments of the invention, filter 25 in breathing tube 24 is included. Filter 25 prevents the entry of foreign bodies into breathing tube 24. According to some preferred embodiments of the invention humidifying element 31 adds moisture to inhaled air passing through breathing tube 24. Most preferably, filter 25 further functions as humidifying element 31. To that end, filter 25 may, for example, retain moisture from exhaled air and transfer the retained moisture to air which is subsequently inhaled.

Optionally, but preferably, a sensor 80 in the breathing tube is further included. Sensor 80 measures at least one parameter selected from the group consisting of an air parameter and a patient parameter as detailed hereinabove.

In order to increase efficiency of device 20, at least one support member 39 positionable beneath a tongue of the human subject is preferably included. Support member 39 functions to aid the human subject in maintaining a correct position of device 20 during use. Support member 39 may be attached to, or integrally formed with, mouthpiece 22. Preferably, support member 39 is at least partially constructed of a flexible material as defined hereinabove. Optionally, but preferably, at least one of the at least one support member 39 is a bifurcated 41 support member 39 (see FIG. 15). As is plainly apparent from FIG. 14, FIG. 15. and FIG. 16, support member 39 may have a surface positionable beneath a tongue of the human subject, and mouthpiece 22 may be said to have a body (also labeled 22) that may be said to pertain to the part of mouthpiece 22 other than support members 39, 41. As is also apparent from FIGS. 14-16, in the case of bifurcated 41 support member 39, each portion of bifurcated 41 support member 39 may comprise substantially elongated members and may comprise substantially planar members.

Optionally, but preferably, an external source of positive pressure 48 is further included. For example, external source of positive pressure 48 may include a pump capable of causing at least one gas to flow through a connecting conduit 43 reversibly engageable by gas exchange port 19. External source of positive pressure 48 may then be employed to inflate positioning aid 34 thereby forming asymmetric protrusion 21. Once inflation is accomplished, disconnection of external source of positive pressure 48 is preferably effected. The present invention, as described hereinabove, constitutes a treatment modality for disorder such as, for example, obstructive sleep apnea (OSA), apnea of infancy (AOI), sudden infant death syndrome (SIDS) and snoring.

According to still another aspect of the present invention there is provided a system for prophylactic treatment of a breathing disorder. The system includes a self contained CPAP device 20 including a mouthpiece 34 insertable in a mouth of a patient. Device 20 further includes a miniature, wearable, battery operated air compressor 45. Device 20 further includes a breathing tube 24 connecting between miniature, wearable, battery operated air compressor 45 and an interior of mouth 28 of the patient.

Miniature, wearable, battery operated air compressor 45 is capable of maintaining sufficient pressure in an upper airway of the patient that collapse of the airway is prevented.

According to an additional aspect of the present invention there is provided an improved method 70 of preventing a breathing disorder by means of CPAP. Method 70 includes inserting 72 mouthpiece 34 in mouth 28 of a patient. Method 70 further includes inflating 74 inflatable positioning aid 34 essentially as described hereinabove. Positioning aid 34 causes mouthpiece 34 to be engaged and retained in a desired position in interior 30 of mouth 28 by means of asymmetric protrusion 21 of positioning aid 34 from mouthpiece 22. Method 70 further includes providing 78 a miniature, wearable, battery operated air compressor 45 as describe hereinabove. Method 70 further includes allowing 80 at least a portion of a flow of air emanating from the miniature, wearable, battery operated air compressor to be inhaled.

According to method 70, a breathing pattern of the patient at least partially regulates a net airflow in an upper airway of the patient. In this way collapse of the upper airway is prevented 82.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A self contained CPAP device to be used by a human patient and for use with a source of positive pressure, comprising:
   a) an inflatable mouthpiece shaped and sized to be inserted into a mouth of a human patient; the inflatable mouthpiece including a non-inflatable tongue support member, the tongue support member having a surface that is positionable beneath a tongue of the human patient in use, the surface spaced apart from a body of the inflatable mouthpiece,
   b) a breathing tube connecting between an outside environment and an interior of said mouth in use, said breathing tube passing through said inflatable mouthpiece, and
   c) an inflatable positioning aid of said inflatable mouthpiece in communication with a gas exchange port allowing said inflatable mouthpiece to be inflatable to adjust said inflatable mouthpiece within said mouth of said human patient at a time when an external source of positive pressure is connected to the gas exchange port, whereas when the external source of positive pressure is disconnected from the gas exchange port gas does not flow to the inflatable positioning aid of the inflatable mouthpiece through the gas exchange port.

2. The device of claim 1, wherein the external source of positive pressure comprises a pump and comprises a connecting conduit reversibly connected to the gas exchange port.

3. The device of claim 1, further comprising a chin holder having a first end which is capable of engaging a chin of said human patient and a second end which is connectable to the device.

4. The device of claim 1, further comprising at least one retaining piece for holding the device in place.

5. The device of claim 1, wherein said inflatable mouthpiece is dimensioned to be inserted a mouth of a human child.

6. The device of claim 1, wherein said inflatable mouthpiece is dimensioned to be inserted in a mouth of a human infant.

7. The device of claim 1, wherein the inflatable mouthpiece includes:
   i) an upper surface that is substantially parallel to a plane defined by said breathing tube;
   ii) a lower surface that is substantially parallel to said plane defined by said breathing tube; and
wherein the inflatable positioning aid comprises an elastic balloon deployed on said upper surface of said inflatable mouthpiece.

8. The device of claim 7 wherein said lower surface is not inflatable and the said inflatable mouthpiece lacks any elastic balloon deployed on said lower surface.

9. The device of claim 1, wherein the tongue support member is bifurcated.

10. The device of claim 9, wherein the surface of the tongue support member includes two substantially elongated members.

11. The device of claim 9, wherein the surface of the tongue support member includes two substantially planar members.

12. A method of preventing collapse of the upper airway, the method comprising:
   a) inserting into a mouth of a human subject a device including an inflatable mouthpiece and a breathing tube connecting between an outside environment and an interior of said mouth in use, said breathing tube passing through said inflatable mouthpiece, the inflatable mouthpiece including a non-inflatable tongue support member, the tongue support member having a surface that is positionable beneath a tongue of the human subject in use, the surface spaced apart from a body of the inflatable mouthpiece; and
   b) using an external source of positive pressure connected to a gas exchange port of the inflatable mouthpiece to inflate an inflatable positioning aid of the inflatable mouthpiece within said mouth to position said inflatable mouthpiece within said mouth so as to prevent collapse of an upper airway of said human subject.

13. The method of claim 12 wherein
   (i) the inflatable mouthpiece includes:
      A) an upper surface that is substantially parallel to a plane defined by said breathing tube;
      B) a lower surface that is substantially parallel to said plane defined by said breathing tube; and (ii) wherein the inflatable positioning aid comprises an elastic balloon deployed between said upper surface and a roof of said mouth of said human subject in use.

14. The method of claim 13 wherein the method is carried out without substantially inflating any element deployed to said lower surface.

15. The method of claim 13 wherein the inflatable positioning aid comprises a plurality of balloons deployed above a plane defined by said breathing tube.

16. The method of claim 13 wherein substantially all said inflating is carried out above said plane defined by said breathing tube.

17. The method of claim 12 wherein
   (i) the inflatable mouthpiece includes:
      A) an upper surface that is substantially parallel to a plane defined by said breathing tube;
      B) a lower surface that is substantially parallel to said plane defined by said breathing tube; and
   (ii) said inserting is carried out such as to place said lower surface in contact with a tongue of said human subject; and
   (iii) said inflating adjusts a position of said lower surface in contact with said tongue to restrict movement of said tongue in a manner that prevents said collapse of said upper airway of said human subject.

18. The method of claim 12 wherein said human subject is a human child.

19. The method of claim 12 wherein said human subject is a human infant.

20. The method of claim 12 wherein the inserting and the inflating is performed so as to prevent at least one of sleep apnea episodes, snoring and sudden infant death syndrome (SIDS) in said human subject.

21. The method of claim 12 wherein:
   i) the method further comprises:
      c) identifying said human subject as in need of treatment of at least one of sleep apnea episodes, snoring and sudden infant death syndrome (SIDS) in said human subject; and
   d) the inserting of said device is carried out in response to said identifying,

* * * * *